US011648239B2

(12) United States Patent
Dobi et al.

(10) Patent No.: US 11,648,239 B2
(45) Date of Patent: *May 16, 2023

(54) AZOPHENOLS AS ERG ONCOGENE INHIBITORS

(71) Applicant: The Henry M. Jackson Foundation for the Advancement of Military Medicine, Inc., Bethesda, MD (US)

(72) Inventors: Albert L. Dobi, Rockville, MD (US); Clifton L. Dalgard, Chevy Chase, MD (US); Shiv K. Srivastava, Potomac, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 98 days.

This patent is subject to a terminal disclaimer.

(21) Appl. No.: 17/158,930

(22) Filed: Jan. 26, 2021

(65) Prior Publication Data

US 2021/0299106 A1    Sep. 30, 2021

Related U.S. Application Data

(63) Continuation of application No. 16/277,410, filed on Feb. 15, 2019, now abandoned, which is a
(Continued)

(51) Int. Cl.
*A61K 31/426* (2006.01)
*C07C 245/00* (2006.01)
(Continued)

(52) U.S. Cl.
CPC ............ *A61K 31/426* (2013.01); *A61K 31/44* (2013.01); *A61K 31/4402* (2013.01);
(Continued)

(58) Field of Classification Search
CPC .. A61K 31/426; A61K 31/44; A61K 31/4402; A61P 35/00; C07D 245/00; C07D 245/02; C07D 245/04; C07D 277/50
See application file for complete search history.

(56) References Cited

U.S. PATENT DOCUMENTS 10,238,639 B2    3/2019    Dobi et al.
2010/0227910 A1    9/2010    Chinnaiyan et al.

FOREIGN PATENT DOCUMENTS

JP       S63159839 A    4/1995
WO    WO 1998/029257   9/1998
(Continued)

OTHER PUBLICATIONS

Anderson, "The Process of Structure-Based Drug Design", Chemistry & Biology, vol. 10, 787-797, Sep. 2003, 11 pages.
(Continued)

*Primary Examiner* — Savitha M Rao
(74) *Attorney, Agent, or Firm* — Sheppard Mullin Richter & Hampton LLP

(57) ABSTRACT

Selective azophenol inhibitors of a wild type or an altered ERG protein expression are described, where the inhibitors represent a compound of Formula (I) or Formula (II)
(Continued)

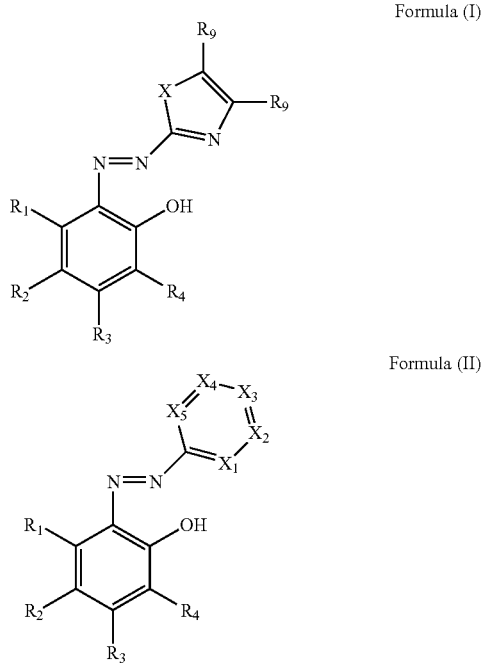

Formula (I)

Formula (II)

wherein X, $X_1$, $X_2$, $X_3$, $X_4$ and $X_5$, $R_1$ through $R_4$ and $R_9$ are as described.

10 Claims, 33 Drawing Sheets

Specification includes a Sequence Listing.

Related U.S. Application Data continuation of application No. 15/561,626, filed as application No. PCT/US2016/051098 on Sep. 9, 2016, now Pat. No. 10,238,639.

(60) Provisional application No. 62/216,839, filed on Sep. 10, 2015.

(51) Int. Cl.
| | | |
|---|---|---|
| *C07C 245/02* | (2006.01) | |
| *C07C 245/04* | (2006.01) | |
| *A61K 31/44* | (2006.01) | |
| *A61K 31/4402* | (2006.01) | |
| *C07D 277/50* | (2006.01) | |
| *A61P 35/00* | (2006.01) | |

(52) U.S. Cl.
CPC ............ *A61P 35/00* (2018.01); *C07C 245/00* (2013.01); *C07C 245/02* (2013.01); *C07C 245/04* (2013.01); *C07D 277/50* (2013.01)

(56) References Cited

FOREIGN PATENT DOCUMENTS

| | | |
|---|---|---|
| WO | WO 2015/048718 A2 | 4/2015 |
| WO | WO 2017/044844 A1 | 3/2017 |

OTHER PUBLICATIONS

Ateeq et al., "Role of dutasteride in pre-clinical ETS fusion-positive prostate cancer models", The Prostate, vol. 72, No. 14, Mar. 13, 2012, pp. 1542-1549, XP055411097.
Brooks et al., "Identification of Potential Prostate Cancer Preventitive Agents Through Induction of Quinone Redutase in Vitro", Cancer Epidemiology, Biomarkers & Prevention, Sep. 2002, vol. 11, pp. 868-875.
Doh-Ura et al., "Chelating Compound, Chrysoidine, Is More Effective in Both Antiprion Activity and Brain Endothelial Permeability Than Quinacrine", Cellular and Molecular Neurobiology, May 2007, vol. 27, No. 3, pp. 303-316.
Extended European Search Report for EP16845184 dated Apr. 4, 2019, 10 pages.
Gusev et al., "Thiazolylazo compounds as analytical reagents for urnanium(VI)", Zhurnal Analiticheskoi KMIMII, vol. 30, No. 3, 1975, pp. 540-544, XP009512158.
International Preliminary Report on Patentability issued in corresponding International Patent Application No. PCT/US2016/051098, dated Mar. 13, 2018, 7 pages.
International Search Report issued in corresponding International Patent Application No. PCT/US2016/051098 dated Feb. 2, 2017.
Ji et al., "Effect of Celastrol on Growth Inhibition of Prostate Cancer Cells through the Regulation of hERG Channel In Vitro", BioMed Reserch International, vol. 2015, Article ID 308475, 7 pages.
Nakamura et al.,"Transition-Metal-Catalyzed Reations in Heterocyclic Synthesis", Chem. Rev. 2004, vol. 104, pp. 2127.
PubChem, Substance Record for SID 162267588 Create Date: May 21, 2013.
PubChem, Substance Record for SID 198947980 Create Date: Aug. 25, 2014.
PubChem, Substance Record for SID 6506557 Create Date: Sep. 14, 2005.
Saitoh, "Solute Partition Study in Aqueous Sodium Dodecyl Sulfate Micellar Solutions for Some Organic Reagents and Metal Chelates", Mikrochimica Acta, 1992, vol. 106, p. 91-99.
Thiel, "Structure-aided drug design's next generation", Nature Biotechnology, vol. 22, No. 5, May 2004, 7 pages.
Wang et al., "Ablation of the oncogenic transcription factor ERG by deubiquitinase inhhibition in prostate cancer", Proceedings of the National Academy of Sciences of the United States of America, vol. 111, No. 11, Mar. 3, 2014, pp. 4251-4256, XP055411107.
Zhou et al., "A study on the adsorption voltammetry of titanium with various heterocyclic azo-compounds", Fresenius' Journal of Analytical Chemistry, 1994, vol. 348, pp. 724-729.

AZOPHENOLS AS ERG ONCOGENE INHIBITORS

CROSS-REFERENCE TO RELATED APPLICATIONS

This application is a Continuation of U.S. patent application Ser. No. 16/277,410, filed Feb. 15, 2019, which is a Continuation of U.S. patent application Ser. No. 15/561,626, filed Sep. 26, 2017, now U.S. Pat. No. 10,238,639, which is a 371 Continuation of PCT/US2016/051098, filed Sep. 9, 2016, which claims priority to U.S. Provisional Application No. 62/216,839, filed Sep. 10, 2015.

STATEMENT REGARDING FEDERALLY SPONSORED RESEARCH OR DEVELOPMENT

This invention was made with government support under HU0001-10-2-0002 and R0704USUS awarded by the Uniformed Services University of the Health Sciences. The government has certain rights in the invention.

SEQUENCE LISTING SUBMISSION VIA EFS-WEB

A computer readable text file, entitled "SequenceListing.txt," created on or about Jul. 11, 2019 with a file size of about 1 kb contains the sequence listing for this application and is hereby incorporated by reference in its entirety.

BACKGROUND OF THE INVENTION

The ETS Related Gene (FRG) proto-oncogene was characterized more than twenty-five years ago (Rao et al., 1987a; Rao el al., 1987b; Reddy et al., 1987) and belongs to a large family of ETS transcription factors that are both positive and negative regulators of gene expression (Watson et al., 2010). These transcription factors are downstream effectors of the mitogenic signal transduction pathways involved in cell proliferation, cell differentiation, development, transformation, apoptosis, and immune regulation (Watson et al., 2010; Sreenath et al., 2011; Dobi et al., 2013).

Prostate cancer (CaP) is the most frequently diagnosed non-skin malignancy and second leading cause of cancer related deaths among men in the western countries, with a projected 1.7 million newly diagnosed cases worldwide (International Agency for Research of Cancer, WHO, Press Release No 209, Mar. 21, 2012). An estimated 2.9 million patients in the United States and 11 million world-wide are currently living with prostate cancer (http://globocan.iarc.fr/old/FactSheets/cancers/prostate-new.asp; http://www.cancer.org/cancer/prostatecancer/detailedguide/prostate-cancer-key-statistics). While early detected CaP due to PSA screening is managed effectively by surgery or radiation, a significant subset of CaP patients (20% to 40%) experience disease recurrence after definitive treatment and will require hormone ablation therapy (Eur. Urol. 2007 May; 51(5): 1175-84, Epub 2007). Despite an initial response to therapy, metastatic CaP tumors eventually become refractory to hormone ablation therapy. For this subset of patients—i.e., those having metastatic hormone refractory cancer, there is no effective cure.

The ERG gene is the most prevalent and validated genomic alteration in prostate cancer The ERG proto-oncogene is overexpressed in 60-70% of prostate tumors in patients of Caucasian ancestry as a result of recurrent gene fusions involving TMPRSS2 and the ETS family of genes (Petrovics et al., 2005; Tomlins et al., 2005; reviewed in Kumar Sinha et al., 2008; Rubin et al., 2012). Emerging studies on human prostate cancer specimens and various experimental models underscore the causative oncogenic function of ERG in prostate cancer (Klezovitch et al., 2008; Tomlins et al., 2008; Sun et al., 2008; Wang et al., 2008). ETS factors reprogram the androgen receptor cistrome and prime prostate tumorigenesis in response to PTEN loss (Chen et al., 2013; Nguyen et al., 2015) Numerous reports have highlighted both diagnostic and prognostic features of the genomic activation of ERG revealing that about half the prostate tumors harbor the most common gene fusion that takes place between the androgen receptor-regulated TMPRSS2 gene promoter and ERG protein coding sequence (reviewed in Kumar-Sinha et al., 2008; Rubin et al., 2012). Fusion between the TMPRSS2 gene promoter and ERG results in the overexpression of N-terminally truncated or full-length forms of ERG (Klezovitch et al., 2008; Sun et al., 2008; Sreenath et al., 2011). Fusion events between ERG and other androgen inducible promoter sequences, such as SLC45A3 (Han et al., 2008) and NDRG1 have also been identified in prostate cancer (Pflueger et al., 2009; Rubin et al., 2012).

ERG expression in CaP is androgen receptor (AR) dependent. While AR signaling inhibitors are employed as therapeutics for treating CaP, compounds that selectively inhibit ERG expression are highly desirable. Up to 4 million of patients living with prostate cancer worldwide are expected to harbor ERG positive tumors (Farrell et al., 2013). Compounds such as ERGi-USU are examples of such selective inhibitors that inhibit the ERG protein in ERG positive cancer cell lines with minimal effect on normal primary endothelial cells that endogenously express ERG—i.e., ERG negative tumor or normal cells (PCT US2015/020172). The azophenols also selectively inhibit ERG expression and thus provide for the treatment of cancers or pathologic conditions associated with an ERG fusion event or ERG overexpression, including, for example, prostate cancer, Ewing's sarcoma, acute myeloid leukemia, megakaryoblastic leukemia, endothelial cancer and acute T-lymphoblastic leukemia.

A systematic screening of 456 known kinases in kinase ligand competition assays (Fabian et al., 2005) indicated potential ligands for RIO2 (Kd=200 nM). The RIO family of atypical serine/threonine kinases was first characterized in 1997 based on the studies of a right open reading frame (RIO1) gene, expressed constitutively at a low level in *Saccharomyces cerevisiae* (Angermayr et al., 1997). Unexpectedly. RIO kinase 2 (RIOK2) protein levels were observed to decrease in ERG expressing VCaP cells in response to the azophenols of the invention with minimal effect on RIOK2 transcript levels as assessed by whole transcriptome analyses. In the present invention, RIOK2 was investigated as a potential target of the ERG inhibitors described herein.

SUMMARY OF THE INVENTION

An aspect of the present invention relates to a method for treating a disease associated with overexpression of wild type ERG protein, an altered ERG protein, ERG gene transcription or ERG mRNA translation in a subject suffering therefrom, comprising administering to the subject a therapeutically effective amount of a compound of Formula (I) or Formula (II)

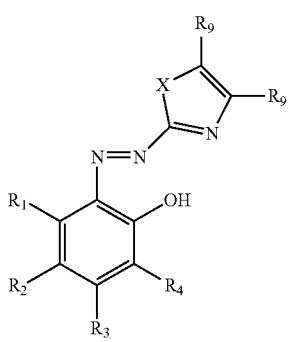

Formula (I)

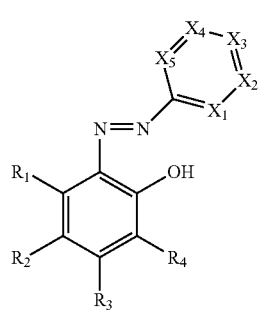

Formula (II)

or a pharmaceutically acceptable salt thereof, wherein:
X is NH, O or S;
$X_1$, $X_2$, $X_3$, $X_4$ and $X_5$ are independently N or $CR_9$, where only one of $X_1$, $X_2$, $X_3$, $X_4$ and $X_5$ is N;
$R_1$, $R_2$ and $R_4$ are independently selected from the group consisting of H, aryl, halogen, $C_1$-$C_{10}$ alkyl, $C_1$-$C_{10}$ alkoxy, $C_3$-$C_7$ cycloalkyl and $C_3$-$C_7$ heterocycloalkyl, wherein the aryl, $C_1$-$C_{10}$ alkyl, $C_1$-$C_{10}$ alkoxy, $C_3$-$C_7$ cycloalkyl and $C_3$-$C_7$ heterocycloalkyl are optionally substituted with one or more substituents selected from the group consisting of $C_1$-$C_8$ alkyl, $C_3$-$C_7$ cycloalkyl, $C_3$-$C_7$ heterocycloalkyl, aryl, heteroaryl, halogen, hydroxyl, —CN, —COOH, —$CF_3$, —$OCH_2F$, —$OCHF_2$, —$OC_1$-$C_8$ alkyl, —O-aryl, —O-heteroaryl, —$NR_5R_6$, —$NR_5C(O)R_6$ and —$C(O)NR_5R_6$;
$R_3$ is selected from the group consisting of H, —OH, —$NR_5R_6$, $C_1$-$C_{10}$ alkyl, $C_1$-$C_{10}$ alkoxy, $C_3$-$C_7$ cycloalkyl and $C_3$-$C_7$ heterocycloalkyl, wherein the $C_1$-$C_{10}$ alkyl, $C_1$-$C_{10}$ alkoxy, $C_3$-$C_7$ cycloalkyl and $C_3$-$C_7$ heterocycloalkyl are optionally substituted with one or more substituents selected from the group consisting of $C_1$-$C_8$ alkyl, $C_3$-$C_7$ cycloalkyl, $C_3$-$C_7$ heterocycloalkyl, aryl, heteroaryl, halogen, hydroxyl, —CN, —COOH, —$CF_3$, —$OCH_2F$, —$OCHF_2$, —$OC_1$-$C_8$ alkyl, —O-aryl, —O-heteroaryl, —$NR_5R_6$, —$NR_5C(O)R_6$ and —$C(O)NR_5R_6$;
$R_5$ and $R_6$ are independently selected from the group consisting of H, $C_1$-$C_8$ alkyl, aryl and $C_3$-$C_7$ cycloalkyl, or $R_5$ and $R_6$ taken together form a $C_3$-$C_7$ heterocycloalkyl wherein the $C_1$-$C_8$ alkyl and $C_3$-$C_7$ heterocycloalkyl are optionally substituted with one or more substituents selected from the group consisting $C_1$-$C_8$ alkyl, $C_3$-$C_7$ cycloalkyl, $C_3$-$C_7$ heterocycloalkyl, aryl, heteroaryl, halogen, hydroxyl, —CN, —COOH, —$CF_3$, —$OCH_2F$, —$OCHF_2$, —$OC_1$-$C_8$ alkyl, —O-aryl, —O-heteroaryl, —$NR_7R_8$, —$NR_7C(O)R_8$ and —$C(O)NR_7R_8$;
$R_7$ and $R_8$ are independently selected from the group consisting of H and $C_1$-$C_8$ alkyl;
each $R_9$ is independently H, halogen, —CN, —OH, COOH, —$NR_{10}R_{11}$, $C_1$-$C_{10}$ alkyl, $C_3$-$C_7$ cycloalkyl, $C_1$-$C_{10}$ alkoxy and $C_3$-$C_7$ heterocycloalkyl wherein the $C_1$-$C_8$ alkyl, $C_3$-$C_7$ cycloalkyl, $C_1$-$C_{10}$ alkoxy and $C_3$-$C_7$ heterocycloalkyl are optionally substituted with one or more substituents selected from the group consisting of $C_1$-$C_8$ alkyl, $C_3$-$C_7$ cycloalkyl, $C_3$-$C_7$ heterocycloalkyl, aryl, heteroaryl, halogen, hydroxyl, —CN, —COOH, —$CF_3$, —$OCH_2F$, —$OCHF_2$, —$OC_1$-$C_8$ alkyl, —O-aryl, —O-heteroaryl, —$NR_{10}R_{11}$, —$NR_{10}C(O)R_{11}$ and —$C(O)NR_{10}R_{11}$;
$R_{10}$ and $R_{11}$ are independently selected from the group consisting of H, $C_1$-$C_8$ alkyl and $C_3$-$C_7$ cycloalkyl, or $R_{10}$ and $R_{11}$ taken together form a $C_3$-$C_7$ heterocycloalkyl wherein the $C_1$-$C_8$ alkyl and $C_3$-$C_7$ heterocycloalkyl are optionally substituted with one or more substituents selected from the group consisting $C_1$-$C_8$ alkyl, $C_3$-$C_7$ cycloalkyl, $C_3$-$C_7$ heterocycloalkyl, aryl, heteroaryl, halo, hydroxyl. —CN, —COOH, —$CF_3$, —$OCH_2F$, —$OCHF_2$, —$OC_1$-$C_8$ alkyl, —O-aryl, —O-heteroaryl, —$NR_{12}R_{13}$, —$NR_{12}C(O)R_{13}$ and —$C(O)NR_{12}R_{13}$; and
$R_{12}$ and $R_{13}$ are independently selected from the group consisting of H and $C_1$-$C_8$ alkyl.

In an aspect of the invention directed to Formula (I), X is S; each $R_9$ is H; and $R_1$, $R_2$, $R_3$ and $R_4$ are independently selected from the group consisting of H and $C_1$-$C_{10}$ alkyl, such as $C_1$-$C_8$ alkyl, such as $C_1$-$C_6$ alkyl, such as methyl, ethyl, isopropyl, butyl, isobutyl or pentyl.

In an aspect of the invention directed to Formula (I), X is S; each $R_9$ is H; and at least one of $R_1$, $R_2$, $R_3$ and $R_4$ is not H.

In an aspect of the invention directed to Formula (I), X is S; each $R_4$ is H; $R_3$ is H; and at least one of $R_1$, $R_2$ and $R_4$ is not H, such as $C_1$-$C_{10}$ alkyl, such as $C_1$-$C_8$ alkyl, such as $C_1$-$C_6$ alkyl, such as methyl, ethyl, isopropyl, butyl, isobutyl or pentyl.

In an aspect of the invention directed to Formula (I), X is S; each $R_9$ is H; $R_4$ is H; and at least one of $R_1$, $R_2$ and $R_3$ is not H, such as $C_1$-$C_{10}$ alkyl, such as $C_1$-$C_8$ alkyl, such as $C_1$-$C_6$ alkyl, such as methyl, ethyl, isopropyl, butyl, isobutyl or pentyl.

In an aspect of the invention directed to Formula (I), X is S; each $R_9$ is H; $R_1$ is H; and at least one of $R_2$, $R_3$ and $R_4$ is not H, such as $C_1$-$C_{10}$ alkyl, such as $C_1$-$C_8$ alkyl, such as $C_1$-$C_6$ alkyl, such as methyl, ethyl, isopropyl, butyl, isobutyl or pentyl.

In an aspect of the invention directed to Formula (I), X is S; each $R_4$ is H; $R_3$ and $R_4$ are each H; and at least one of $R_1$ and $R_2$ is not H, such as $C_1$-$C_{10}$ alkyl, such as $C_1$-$C_8$ alkyl, such as $C_1$-$C_6$ alkyl, such as methyl, ethyl, isopropyl, butyl, isobutyl or pentyl.

In an aspect of the invention directed to Formula (I), X is S; each $R_9$ is H; $R_1$, $R_3$ and $R_4$ are each H; and $R_2$ is not H, such as $C_1$-$C_{10}$ alkyl, such as $C_1$-$C_8$ alkyl, such as $C_1$-$C_6$ alkyl, such as methyl, ethyl, isopropyl, butyl, isobutyl or pentyl.

In an aspect of the invention directed to Formula (I), X is S; each $R_9$ is H; $R_1$, $R_3$ and $R_4$ are each H; and $R_2$ is halogen. In a particular embodiment, $R_2$ is fluorine, bromine or chlorine.

In an aspect of the invention directed to Formula (I), X is S; each $R_9$ is H; each of $R_2$ and $R_4$ is H; $R_1$ is methyl, and $R_3$ is OH.

In an aspect of the invention directed to Formula (I), X is S; each $R_9$ is H; each of $R_1$, $R_2$ and $R_4$ is H; and $R_3$ is OH.

In an aspect of the invention directed to Formula (I), X is NH; each $R_9$ is H; each of $R_1$, $R_2$ and $R_4$ is H; $R_1$ is methyl; and $R_3$ is OH.

In an aspect of the invention directed to Formula (I), X is NH; each $R_9$ is H; each of $R_1$, $R_3$ and $R_4$ is H; and $R_2$ is methyl or isopropyl.

In an aspect of the invention directed to Formula (I), X is O; each $R_9$ is H; each of $R_1$, $R_3$ and $R_4$ is H; and $R_2$ is methyl or isopropyl.

In an aspect of the invention directed to Formula (I), X is O; each $R_9$ is H; each of $R_1$, $R_2$ and $R_4$ is H; and $R_3$ is OH.

In an aspect of the invention directed to Formula (II), $X_1$ is N; $X_2$, $X_3$, $X_4$ and $X_5$ are $CR_9$; each $R_9$ is H; each of $R_1$, $R_2$ and $R_4$ is H; and $R_3$ is OH.

In an aspect of the invention directed to Formula (II), $X_1$ is N; $X_2$, $X_3$, $X_4$ and $X_5$ are $CR_9$; each $R_9$ is H; each of $R_1$, $R_3$ and $R_4$ is H; and $R_2$ is halogen. In a particular embodiment, $R_2$ is fluorine, bromine or chlorine.

In an aspect of the invention directed to Formula (II), $X_1$ is N, $X_2$, $X_3$, $X_4$ and $X_5$ are $CR_9$; each $R_9$ is H; each of $R_2$ and $R_4$ is H; $R_1$ is methyl; and $R_3$ is OH.

In an aspect of the invention directed to Formula (II), $X_1$ is N, $X_2$, $X_3$, $X_4$ and $X_5$ are $CR_9$; each $R_9$ is H; each of $R_1$, $R_2$ and $R_4$ is H; $R_3$ is $NR_5R_6$; and $R_5$ and $R_6$ are each independently $C_1$-$C_8$ alkyl, such as methyl, ethyl, isopropyl, butyl, isobutyl, pentyl or hexyl.

In an aspect of the invention directed to Formula (II), $X_2$ is N; $X_1$, $X_3$, $X_4$ and $X_5$ are $CR_9$; each $R_9$ is H; each of $R_1$, $R_2$ and $R_4$ is H; and $R_3$ is OH.

In an aspect of the invention directed to Formula (II), $X_2$ is N; $X_1$, $X_3$, $X_4$ and $X_5$ are $CR_9$; each $R_9$ is H; each of $R_1$, $R_2$ and $R_4$ is H; $R_3$ is $NR_5R_6$; and $R_5$ and $R_6$ are each independently $C_1$-$C_8$ alkyl, such as methyl, ethyl, isopropyl, butyl, isobutyl, pentyl or hexyl.

In an aspect of the invention directed to Formula (II), $X_3$ is N; $X_1$, $X_2$, $X_4$ and $X_5$ are $CR_9$; each $R_9$ is H; each of $R_1$, $R_2$ and $R_4$ is H; and $R_3$ is OH.

In an aspect of the invention directed to Formula (II), $X_3$ is N; $X_1$, $X_2$, $X_4$ and $X_5$ are $CR_9$; each $R_9$ is H; each of $R_1$, $R_2$ and $R_4$ is H; $R_3$ is $NR_5R_6$; and $R_5$ and $R_6$ are each independently $C_1$-$C_8$ alkyl, such as methyl, ethyl, isopropyl, butyl, isobutyl, pentyl or hexyl.

In an aspect of the invention directed to Formula (II), $X_1$ is N; $X_2$, $X_3$, $X_4$ and $X_5$ are $CR_9$, where the $R_9$ at position $X_3$ is halogen and the $R_9$ at each of positions $X_2$, $X_4$ and $X_5$ is H; each of $R_1$, $R_2$ and $R_4$ is H; and $R_3$ is OH. In a particular embodiment, the halogen at $X_3$ is F, Cl or Br, such as Br.

In an aspect of the invention directed to Formula (II), $X_1$ is N; $X_2$, $X_3$, $X_4$ and $X_5$ are $CR_9$, where the $R_9$ at position $X_3$ is halogen and the $R_9$ at each of positions $X_2$, $X_4$ and $X_5$ is H; each of $R_1$, $R_2$ and $R_4$ is H; $R_3$ is $NR_5R_6$; and $R_5$ and $R_6$ are each independently $C_1$-$C_8$ alkyl, such as methyl, ethyl, isopropyl, butyl, isobutyl pentyl or hexyl. In a particular embodiment, the halogen at $X_3$ is F, Cl or Br, such as Br.

In an aspect of the invention directed to Formula (II), $X_1$ is N; $X_2$, $X_3$, $X_4$ and $X_5$ are $CR_9$, where the $R_9$ at position $X_2$ is halogen and the $R_9$ at each of positions $X_3$, $X_4$ and $X_5$ is H; each of $R_1$, $R_2$ and $R_4$ is H; and $R_1$ is OH. In a particular embodiment, the halogen at $X_2$ is F, Cl or Br, such as Br.

In an aspect of the invention directed to Formula (II), $X_1$ is N; $X_2$, $X_3$, $X_4$ and $X_5$ are $CR_9$, where the $R_9$ at position $X_2$ is halogen and the $R_9$ at each of positions $X_3$, $X_4$ and $X_5$ is H; each of $R_1$, $R_2$ and $R_4$ is H; $R_3$ is $NR_5R_6$; and $R_5$ and $R_6$ are each independently $C_1$-$C_8$ alkyl, such as methyl, ethyl, isopropyl, butyl, isobutyl, pentyl or hexyl. In a particular embodiment, the halogen at $X_2$ is F, Cl or Br, such as Br.

In an aspect of the invention directed to Formula (II), $X_1$ is N; $X_2$, $X_3$, $X_4$ and $X_5$ are $CR_9$, where the $R_9$ at position $X_4$ is halogen and the $R_9$ at each of positions $X_2$, $X_3$ and $X_5$ is H; each of $R_1$, $R_2$ and $R_4$ is H; and $R_3$ is OH In a particular embodiment, the halogen at $X_4$ is F, Cl or Br, such as Br.

In an aspect of the invention directed to Formula (II), $X_1$ is N; $X_2$, $X_3$, $X_4$ and $X_5$ are $CR_9$, where the $R_9$ at position $X_4$ is halogen and the $R_9$ at each of positions $X_2$, $X_3$ and $X_5$ is H; each of $R_1$, $R_2$ and $R_4$ is H; $R_3$ is $NR_5R_6$; and $R_5$ and $R_6$ are each independently $C_1$-$C_8$ alkyl, such as methyl, ethyl, isopropyl, butyl, isobutyl, pentyl or hexyl. In a particular embodiment, the halogen at $X_4$ is F, Cl or Br, such as Br.

In an aspect of the invention directed to Formula (II), $X_1$ is N; $X_2$, $X_3$, $X_4$ and $X_5$ are $CR_9$, where the $R_9$ at position $X_5$ is halogen and the $R_9$ at each of positions $X_2$, $X_3$ and $X_4$ is H; each of $R_1$, $R_2$ and $R_4$ is H; and $R_3$ is OH. In a particular embodiment, the halogen at $X_5$ is F, Cl or Br, such as Br.

In an aspect of the invention directed to Formula (II), $X_1$ is N; $X_2$, $X_3$, $X_4$ and $X_5$ are $CR_9$, where the $R_9$ at position $X_5$ is halogen and the $R_9$ at each of positions $X_2$, $X_3$ and $X_4$ is H; each of $R_1$, $R_2$ and $R_4$ is H; $R_3$ is $NR_5R_6$; and $R_5$ and $R_6$ are each independently $C_1$-$C_8$ alkyl, such as methyl, ethyl, isopropyl, butyl, isobutyl, pentyl or hexyl. In a particular embodiment, the halogen at $X_5$ is F, Cl or Br, such as Br.

In an aspect of the invention, the compound of Formula (I) is a compound of Formula (III)

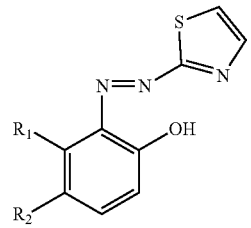

Formula (III)

or a pharmaceutically acceptable salt thereof, wherein $R_1$ and $R_2$ are as defined for Formula (I).

In an aspect of the invention, $R_1$ and $R_2$ of Formula (III) are independently selected from the group consisting of H, $C_1$-$C_6$ alkyl, such as $C_1$-$C_4$ alkyl, such as methyl, ethyl, isopropyl, butyl and isobutyl, where at least one of $R_1$ and $R_2$ is not H.

In an aspect of the invention, $R_1$ of Formula (III) is H and $R_2$ is $C_1$-$C_6$ alkyl, such as $C_1$-$C_4$ alkyl, such as methyl, ethyl, isopropyl, butyl or isobutyl.

In an aspect of the invention, $R_1$ of Formula (III) is H and $R_2$ is $C_1$-$C_6$ alkyl.

In an aspect of the invention, the compound of Formula (I) is

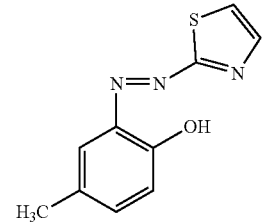

or a pharmaceutically acceptable salt thereof.

In an aspect of the invention, the compound of Formula (I) is

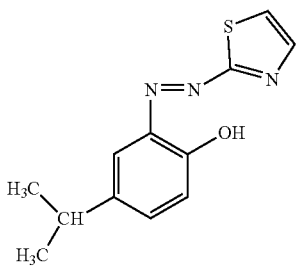 [SMILES: CC(C)c1ccc(O)c(/N=N/c2nccs2)c1]

or a pharmaceutically acceptable salt thereof.

In an aspect of the invention, the compound of Formula (II) is a compound of Formula (IV)

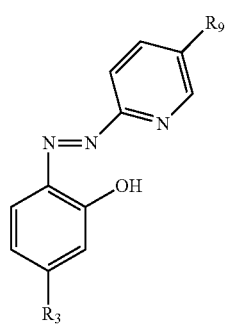

Formula (IV)

or a pharmaceutically acceptable salt thereof,
wherein $R_3$ and $R_9$ are as defined for Formula (II).

In an aspect of the invention, the compound of Formula (IV) is

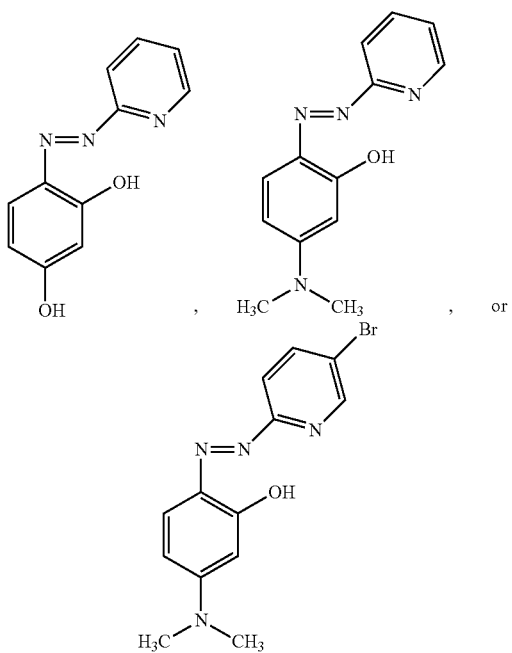

or a pharmaceutically acceptable salt thereof.

In an aspect of the invention, the compounds of Formulae (I), (II), (III), (IV) and (V) are effective in treating a disease selected from the group consisting of prostate cancer, Ewing's sarcoma, acute myeloid leukemia, acute T-lymphoblastic leukemia, endothelial cancer and colon cancer.

In an aspect of the invention, the disease is prostate cancer.

Another aspect of the invention is a compound of Formula (V)

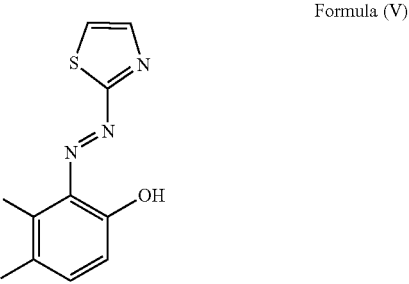

Formula (V)

or a pharmaceutically acceptable salt thereof, wherein $R_1$ is selected from the group consisting of H and optionally substituted $C_1$-$C_{10}$ alkyl, such as $C_1$-$C_9$ alkyl, such as $C_1$-$C_8$ alkyl, such as $C_1$-$C_7$ alkyl, such as $C_1$-$C_6$ alkyl, such as $C_1$-$C_5$ alkyl, such as methyl, ethyl, isopropyl, butyl and isobutyl; and $R_2$ is optionally substituted $C_2$-$C_{10}$ alkyl, such as $C_2$-$C_8$ alkyl, such as $C_2$-$C_7$ alkyl, such as $C_2$-$C_6$ alkyl, such as $C_2$-$C_5$ alkyl, such as $C_2$-$C_4$ alkyl, such as isopropyl, butyl and isobutyl, with the proviso that when $R_1$ is H, $R_2$ is not ethyl, isobutyl or —C(CH$_3$)$_2$—CH$_2$—C(CH$_3$)$_3$.

In an aspect of the invention, $R_1$ is H and $R_2$ is optionally substituted $C_2$-$C_{10}$ alkyl, with the proviso that $R_2$ is not ethyl, isobutyl or —C(CH$_3$)$_2$—CH$_2$—C(CH$_3$)$_3$.

In an aspect of the invention, the compound of Formula (V) is

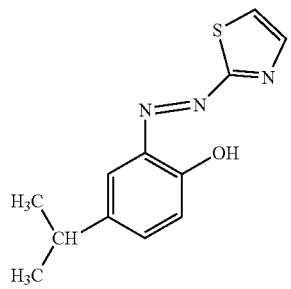 [SMILES: CC(C)c1ccc(O)c(/N=N/c2nccs2)c1]

or a pharmaceutically acceptable salt thereof.

An aspect of the invention is a method for treating a disease associated with overexpression of wild type ERG protein, an altered ERG protein, ERG gene transcription or ERG mRNA translation in a subject suffering therefrom, comprising administering to the subject a therapeutically effective amount of a compound of Formula (V)

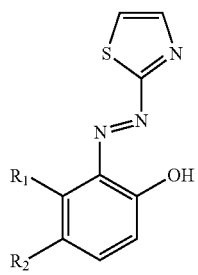

Formula (V)

or a pharmaceutically acceptable salt thereof, wherein:
$R_1$ and $R_2$ are as defined for Formula (V).

In an aspect of the invention, the disease is prostate cancer.

Another aspect of the invention is a pharmaceutical composition comprising the compound of Formula (I) and an excipient.

Another aspect of the invention is a pharmaceutical composition comprising the compound of Formula (II) and an excipient.

Another aspect of the invention is a pharmaceutical composition comprising the compound of Formula (III) and an excipient.

Another aspect of the invention is a pharmaceutical composition comprising the compound of Formula (IV) and an excipient.

Another aspect of the invention is a pharmaceutical composition comprising the compound of Formula (V) and an excipient.

An aspect of the invention is a method for treating a disease associated with overexpression of wild type ERG protein, an altered ERG protein, ERG gene transcription or ERG mRNA translation in a subject suffering therefrom, comprising administering to the subject a therapeutically effective amount of a pharmaceutical composition comprising a compound of Formula (I) and an excipient.

An aspect of the invention is a method for treating a disease associated with overexpression of wild type ERG protein, an altered ERG protein, ERG gene transcription or ERG mRNA translation in a subject suffering therefrom, comprising administering to the subject a therapeutically effective amount of a pharmaceutical composition comprising a compound of Formula (II) and an excipient.

An aspect of the invention is a method for treating a disease associated with overexpression of wild type ERG protein, an altered ERG protein, ERG gene transcription or ERG mRNA translation in a subject suffering therefrom, comprising administering to the subject a therapeutically effective amount of a pharmaceutical composition comprising a compound of Formula (III) and an excipient.

An aspect of the invention is a method for treating a disease associated with overexpression of wild type ERG protein, an altered ERG protein, ERG gene transcription or ERG mRNA translation in a subject suffering therefrom, comprising administering to the subject a therapeutically effective amount of a pharmaceutical composition comprising a compound of Formula (IV) and an excipient.

An aspect of the invention is a method for treating a disease associated with overexpression of wild type ERG protein, an altered ERG protein, ERG gene transcription or ERG mRNA translation in a subject suffering therefrom, comprising administering to the subject a therapeutically effective amount of a pharmaceutical composition comprising a compound of Formula (V) and an excipient.

An aspect of the invention is a method for treating a disease associated with overexpression of wild type ERG protein, an altered ERG protein, ERG gene transcription or ERG mRNA translation in a subject suffering therefrom, comprising co-administering to the subject a therapeutically effective amount of a compound of Formula (I) in combination with a therapeutically effective amount of a known ERG inhibitor.

An aspect of the invention is a method for treating a disease associated with overexpression of wild type ERG protein, an altered ERG protein, ERG gene transcription or ERG mRNA translation in a subject suffering therefrom, comprising co-administering to the subject a therapeutically effective amount of a compound of Formula (II) in combination with a therapeutically effective amount of a known ERG inhibitor.

An aspect of the invention is a method for treating a disease associated with overexpression of wild type ERG protein, an altered ERG protein, ERG gene transcription or ERG mRNA translation in a subject suffering therefrom, comprising co-administering to the subject a therapeutically effective amount of a compound of Formula (III) in combination with a therapeutically effective amount of a known ERG inhibitor.

An aspect of the invention is a method for treating a disease associated with overexpression of wild type ERG protein, an altered ERG protein, ERG gene transcription or ERG mRNA translation in a subject suffering therefrom, comprising co-administering to the subject a therapeutically effective amount of a compound of Formula (IV) in combination with a therapeutically effective amount of a known ERG inhibitor.

An aspect of the invention is a method for treating a disease associated with overexpression of wild type ERG protein, an altered ERG protein, ERG gene transcription or ERG mRNA translation in a subject suffering therefrom, comprising co-administering to the subject a therapeutically effective amount of a compound of Formula (V) in combination with a therapeutically effective amount of a known ERG inhibitor.

BRIEF DESCRIPTION OF THE DRAWINGS

The following figures are merely representative of selected embodiments of the present invention and are not intended to define or narrow the scope of the invention as otherwise described herein. The chemical structures of Compounds 1 to 7 referred to in the Figures below are depicted in FIG. 1A.

DETAILED DESCRIPTION

Definitions

Figure 1A:
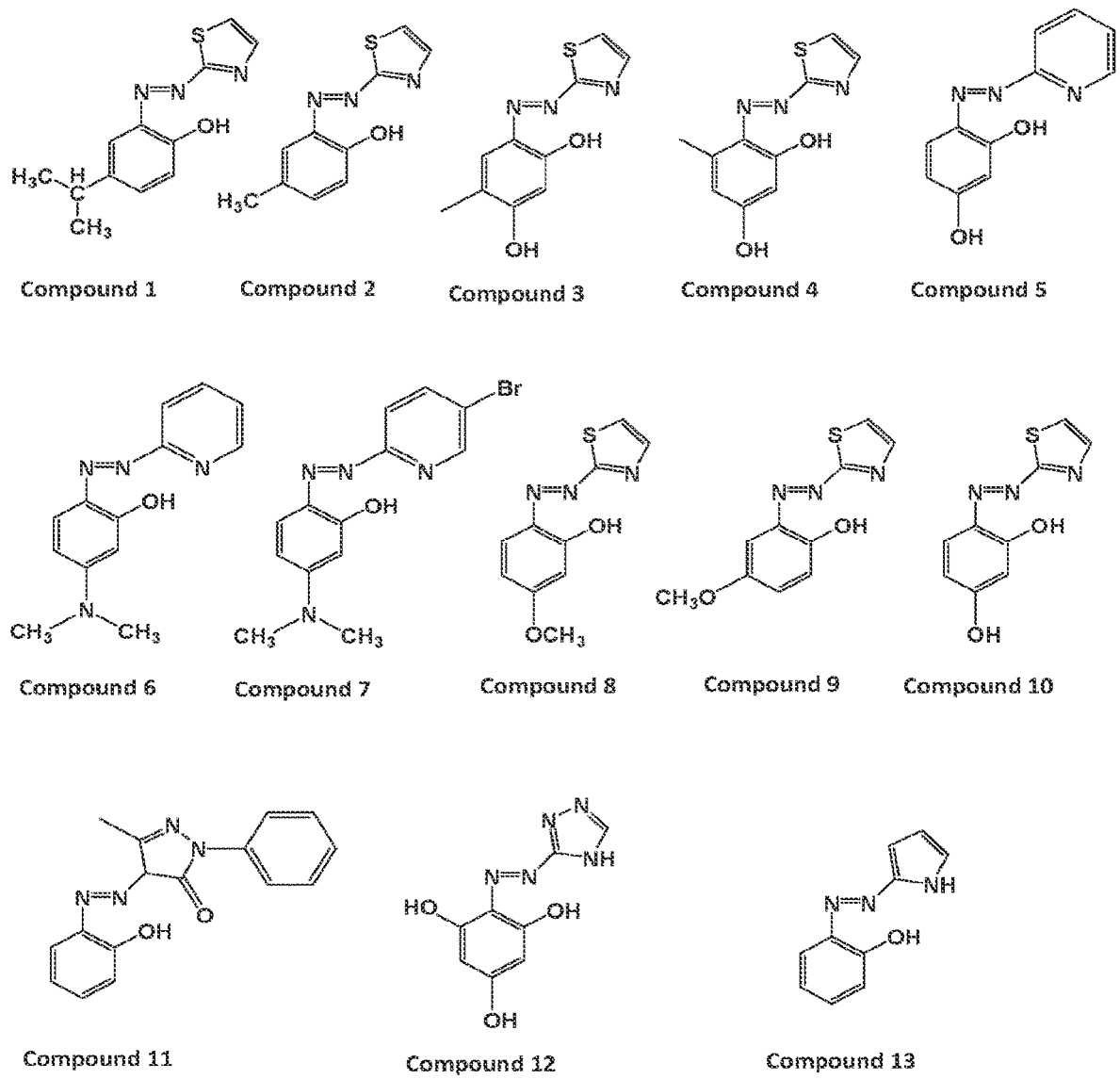
FIG. 1A depicts the azophenol compounds 1-13 for which testing as ERG inhibitors is disclosed herein.
Figure 1B:
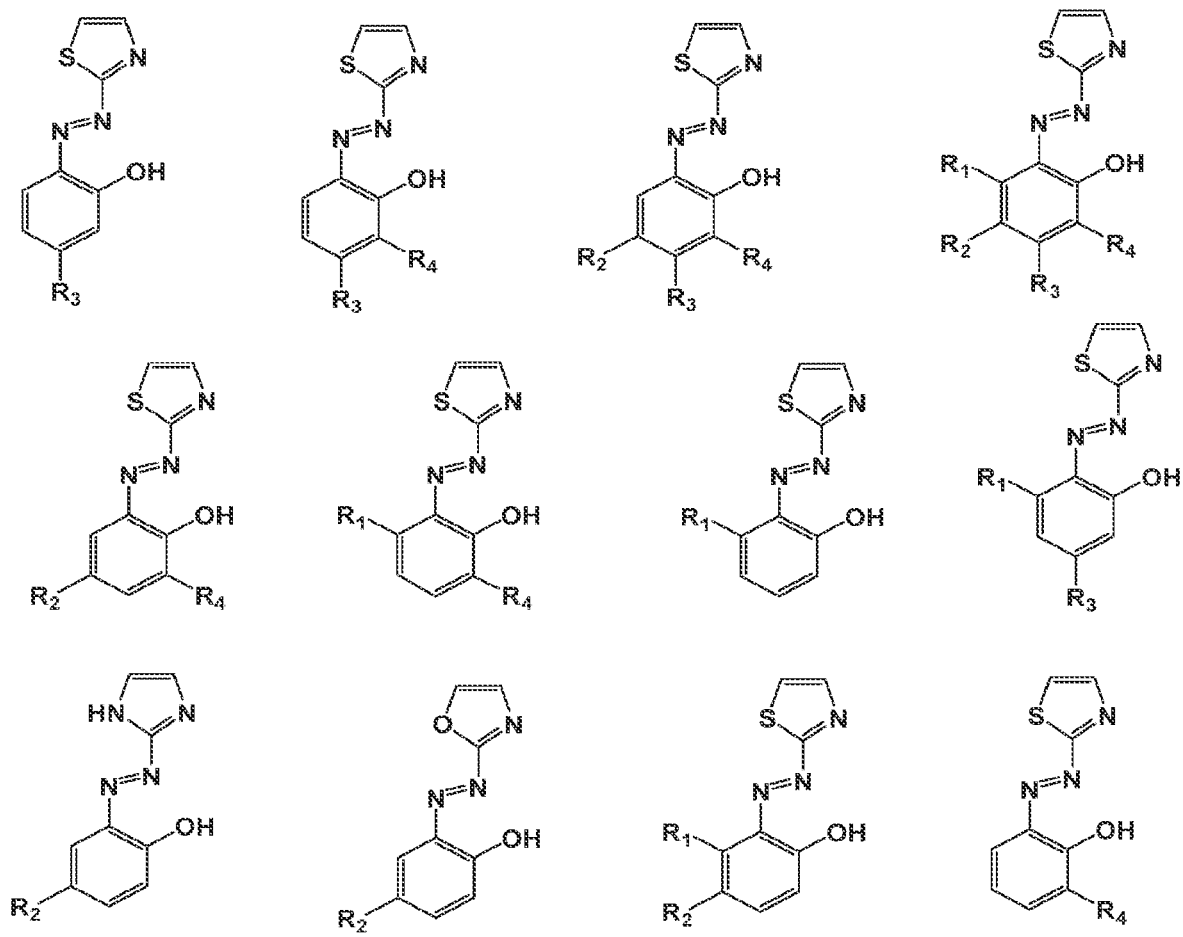
FIG. 1B represents exemplary substitution patterns for the compounds of Formula (I) as described herein.
Figure 1C:
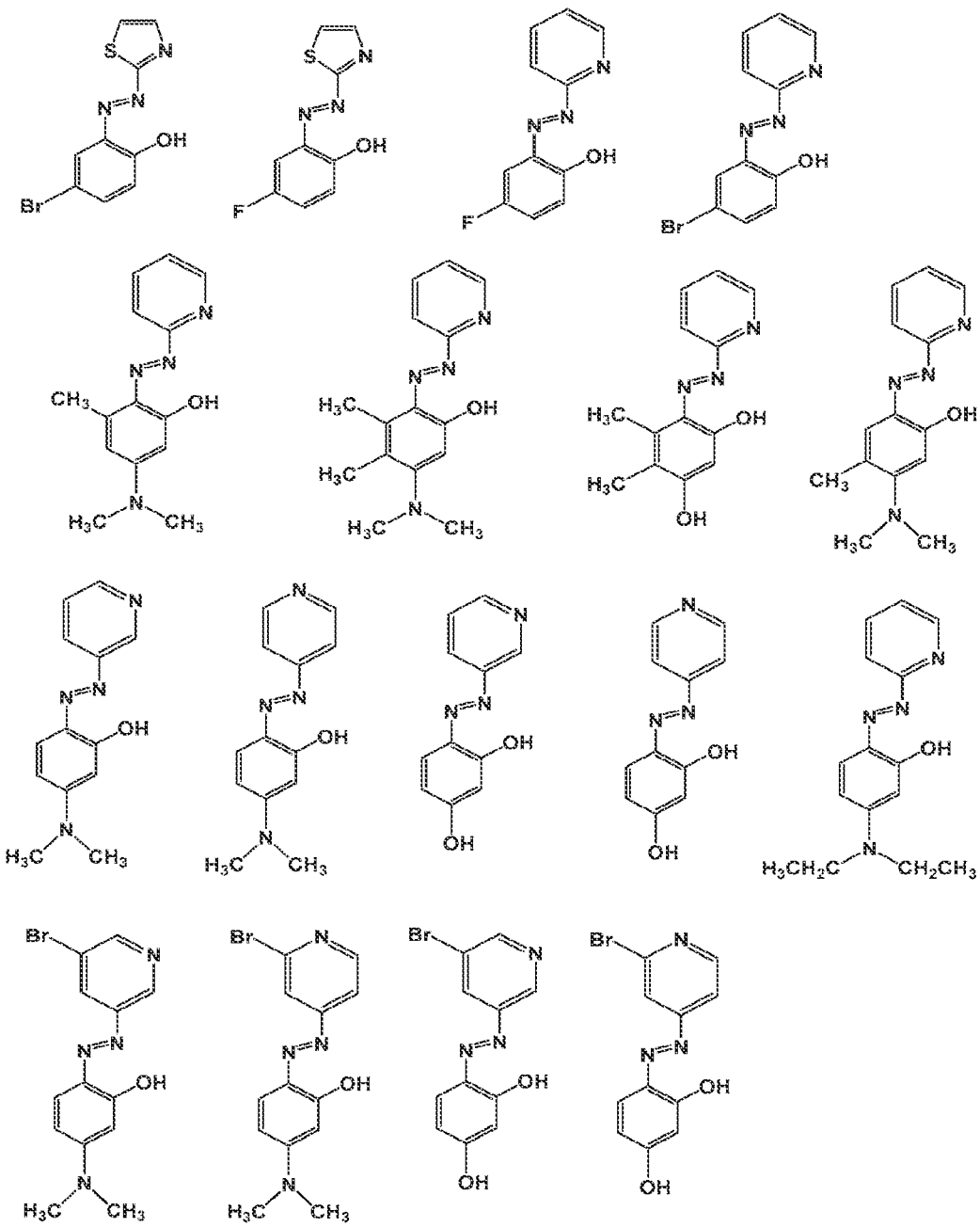
FIGS. 1C and 1D depict the chemical structures of exemplary azophenol compounds of Formula (I) and Formula (II) as described herein.
Figure 1D:
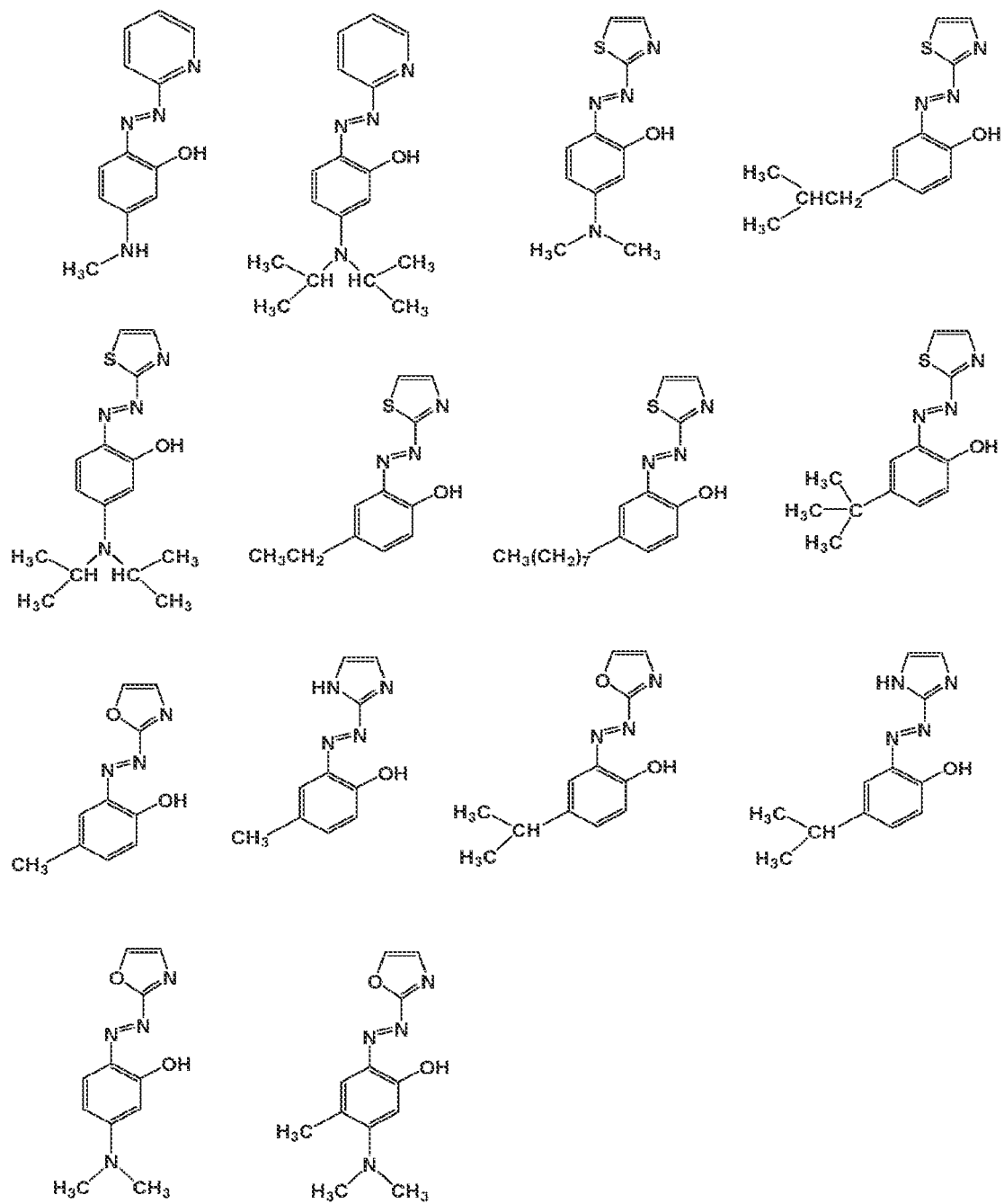
Figure 2:
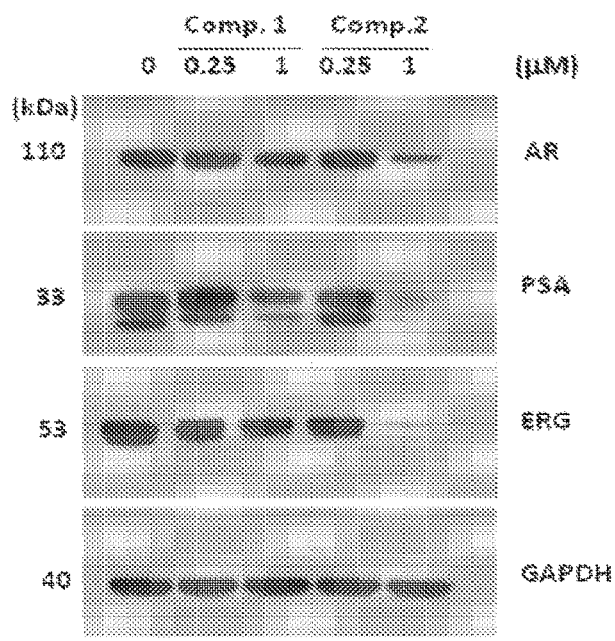
FIG. 2 illustrates the inhibition of endogenous AR, PSA and ERG proteins in ERG harboring prostate cancer cells (VCaP) by Compounds 1 and 2 at concentrations of 0.25 μM and 1 μM.
Figure 2:
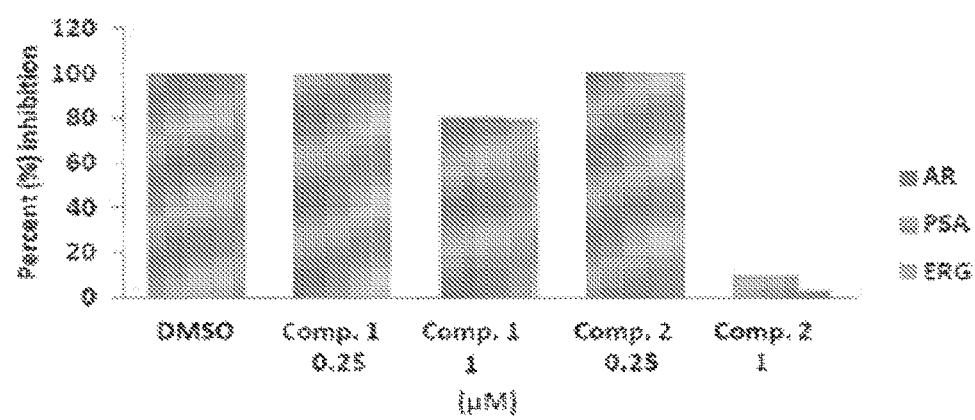
Figure 3:
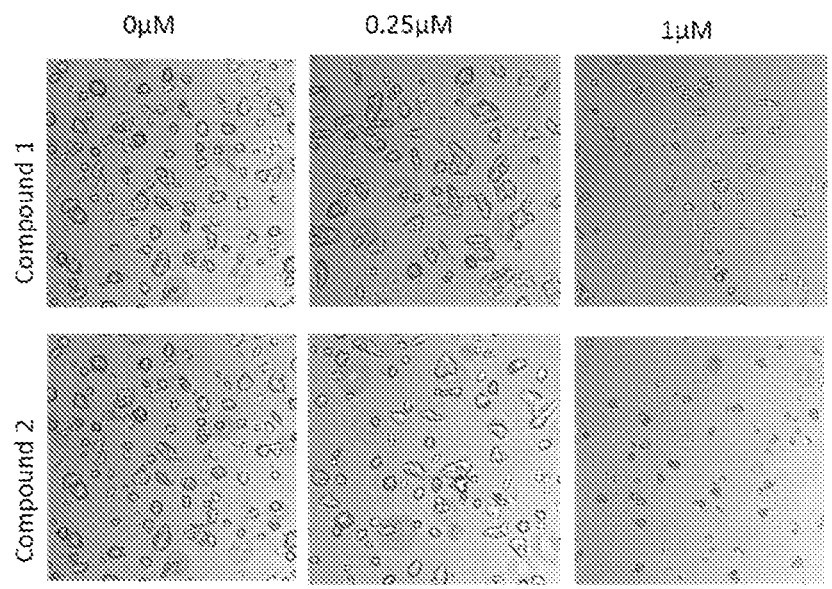
FIG. 3 illustrates the inhibition of the growth of ERG harboring prostate cancer cells (VCaP) by the Compounds 1 and 2 at concentrations of 0.25 μM and 1 μM.
Figure 3:
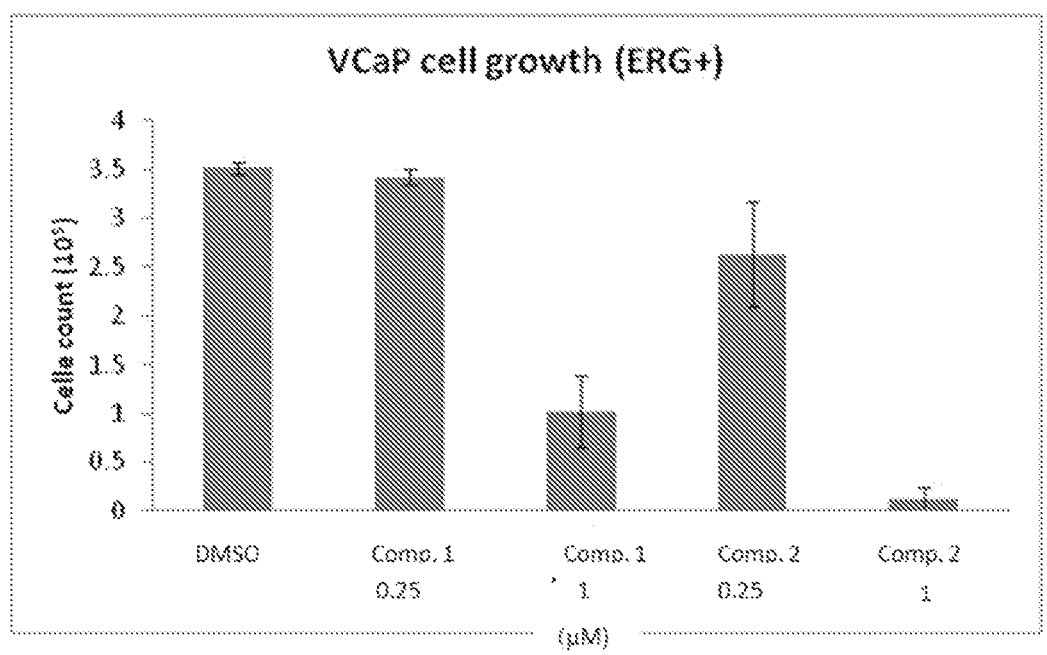
Figure 4:
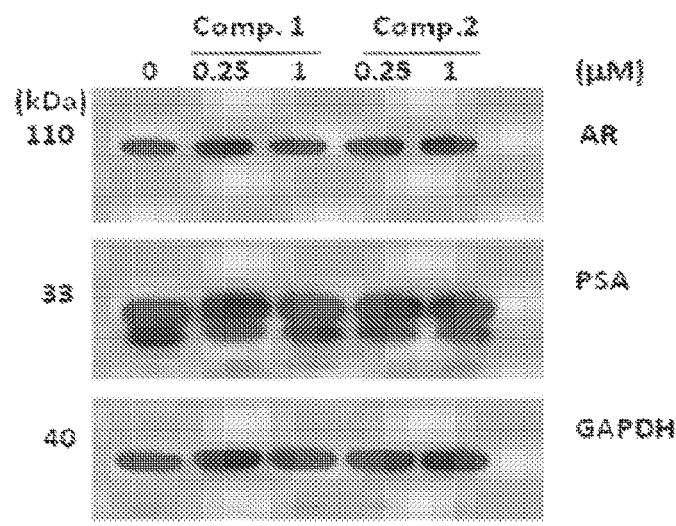
FIG. 4 illustrates the lack of inhibition of endogenous AR and PSA proteins in ERG negative prostate cancer cells (LNCaP) by Compounds 1 and 2 at concentrations of 0.25 μM and 1 μM.
Figure 4:
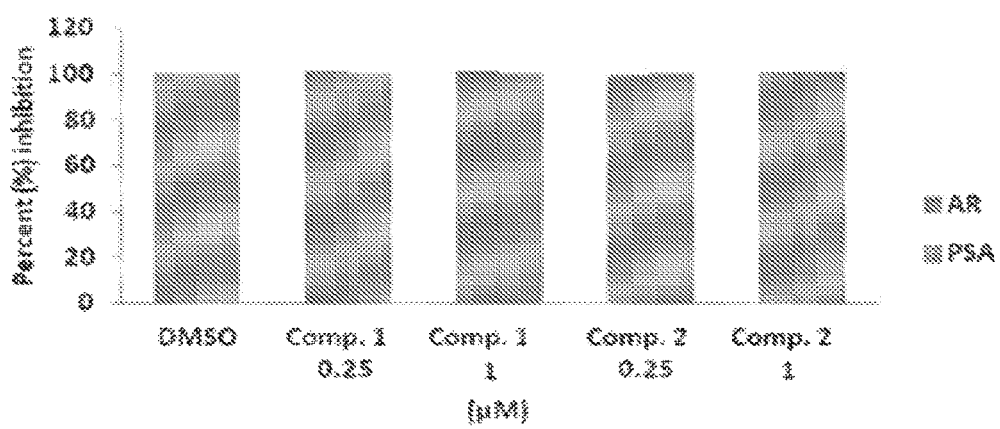
Figure 5:
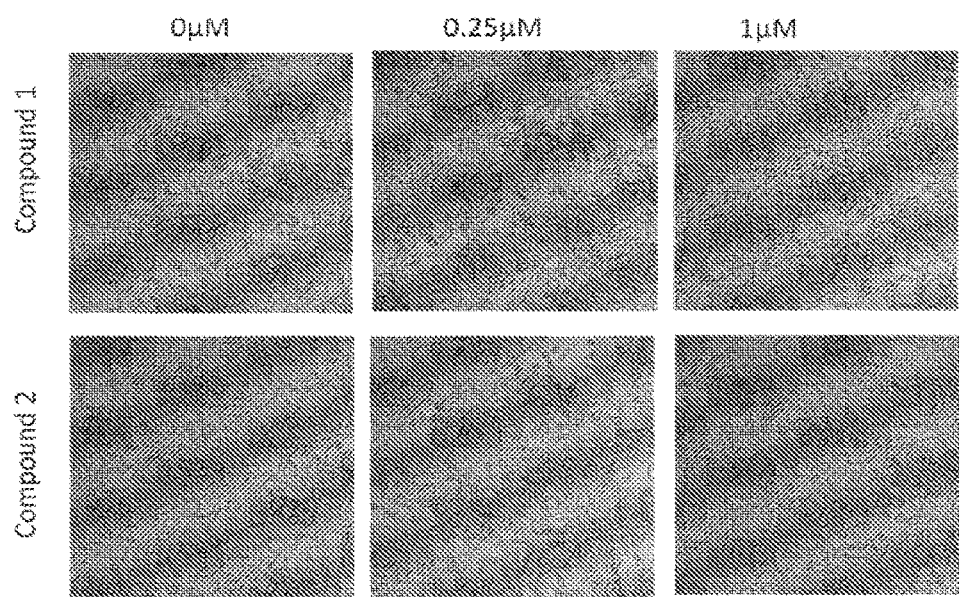
FIG. 5 illustrates that Compounds 1 and 2 at concentrations of 0.25 μM and 1 μM do not affect the growth of ERG negative prostate cancer cells (LNCaP).
Figure 5:
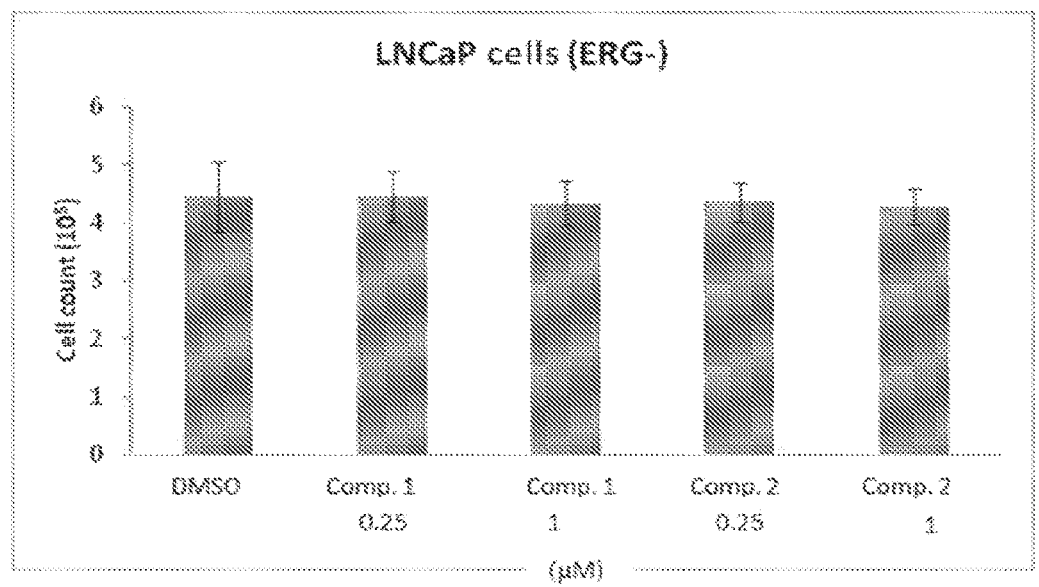
Figure 6:
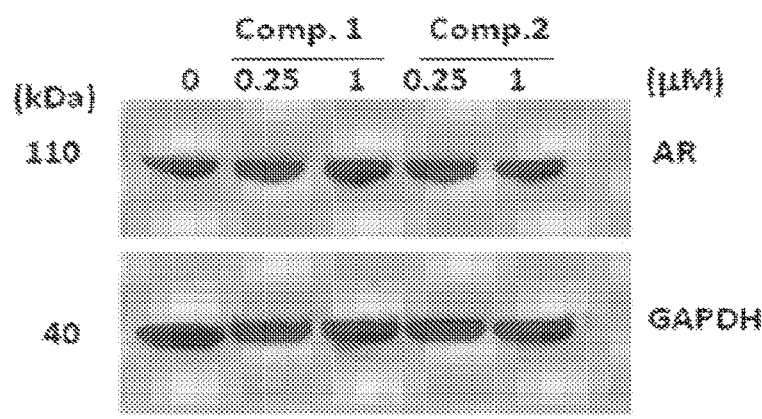
FIG. 6 illustrates that Compounds 1 and 2 at concentrations of 0.25 μM and 1 μM do not inhibit endogenous AR protein in ERG negative prostate cancer cells (LAPC-4).
Figure 6:
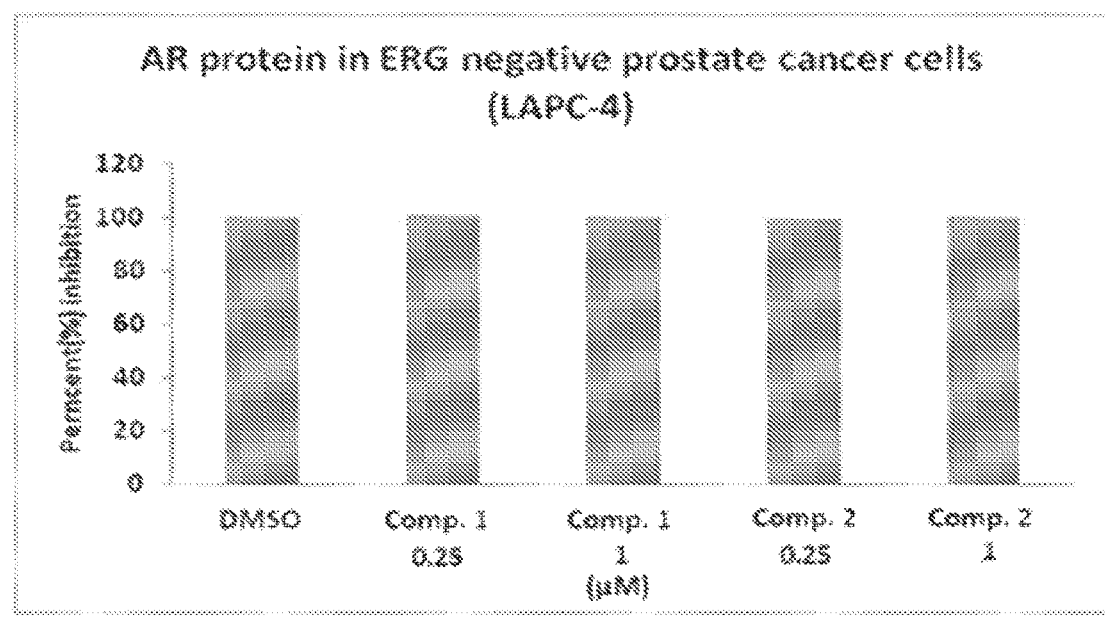
Figure 7:
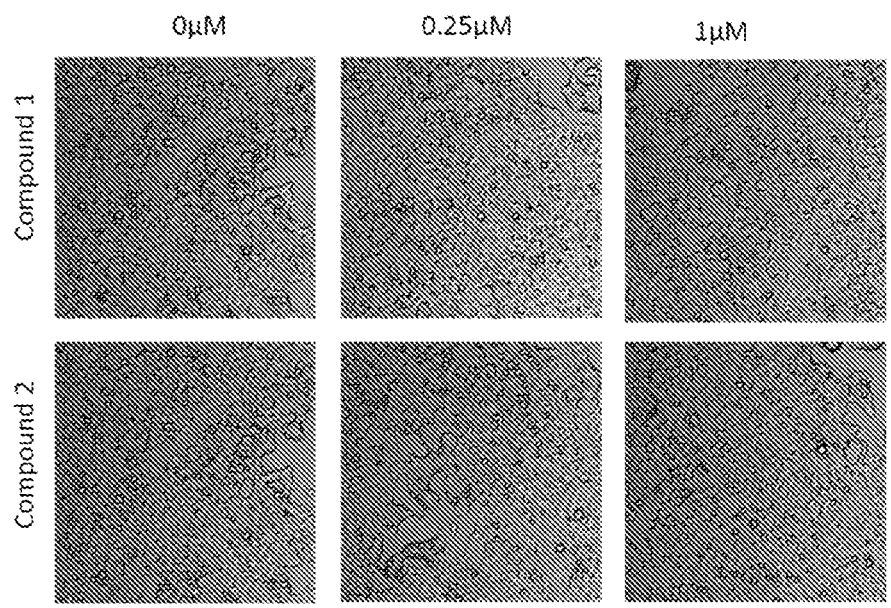
FIG. 7 illustrates that Compounds 1 and 2 at concentrations of 0.25 μM and 1 μM do not affect the growth of ERG negative prostate cancer cells (LAPC-4).
Figure 7:
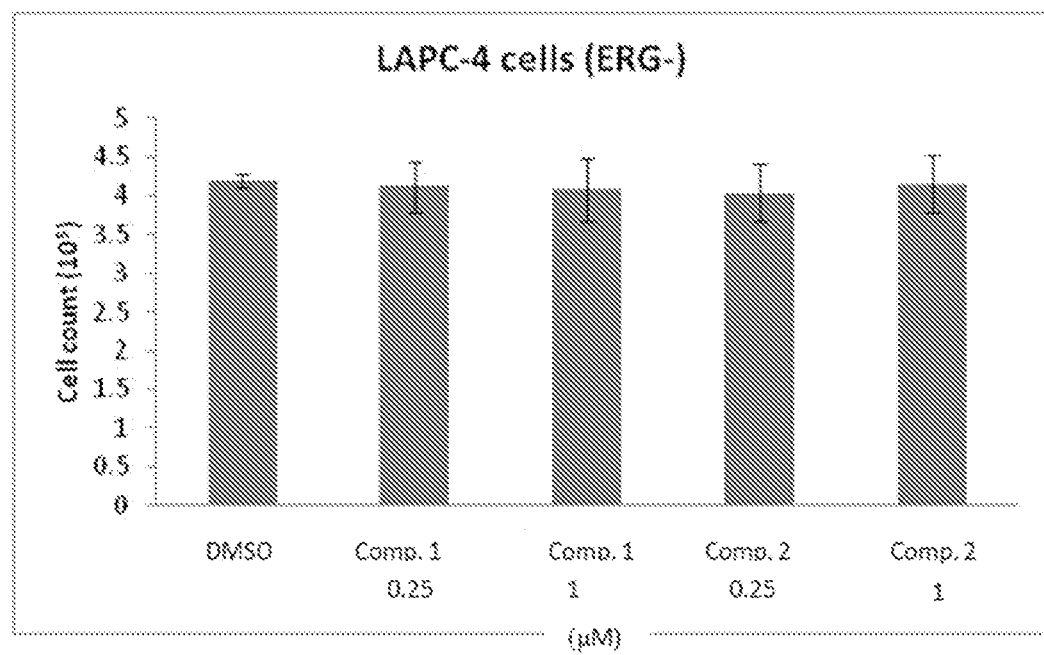
Figure 8:
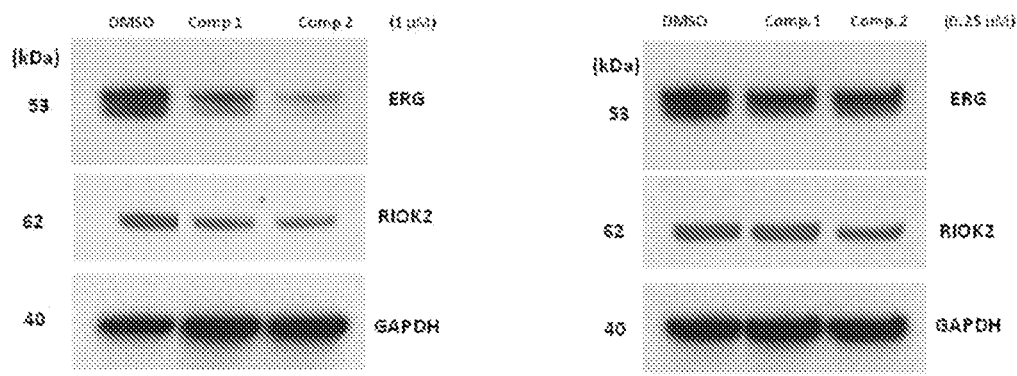
FIG. 8 illustrates the inhibition of endogenous ERG and RIOK2 proteins in ERG harboring cancer cells (COLO320) by Compounds 1 and 2 at concentrations of 0.25 μM and 1 μM.
Figure 8:
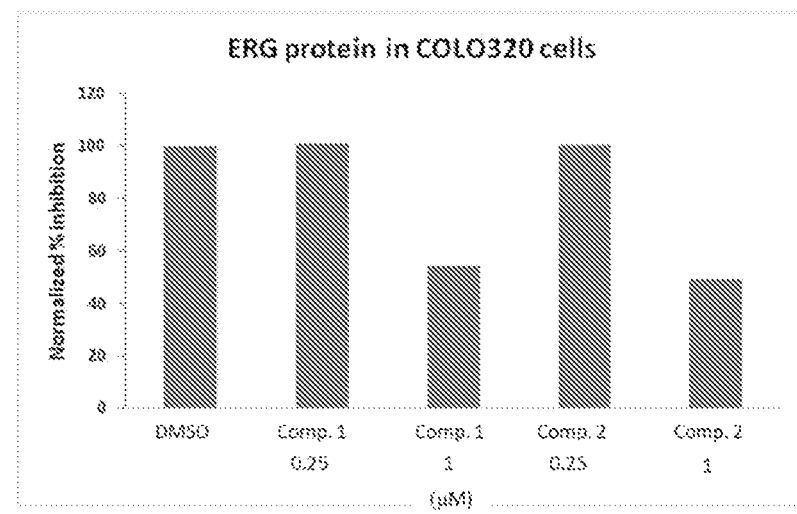
Figure 8:
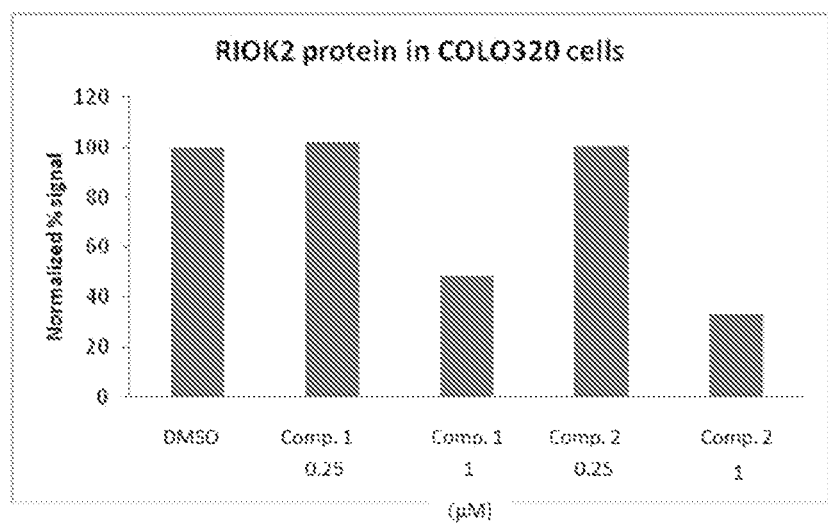
Figure 9:
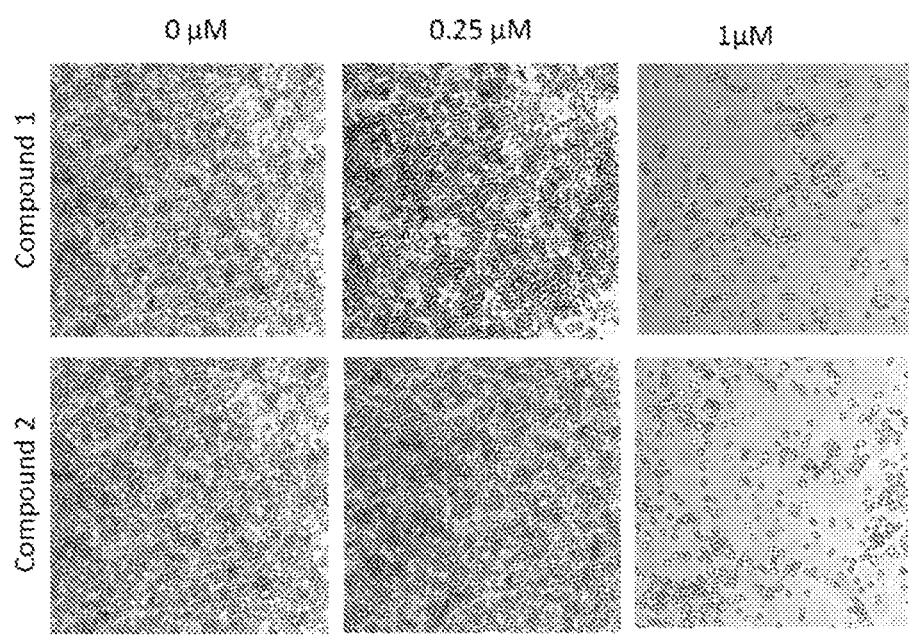
FIG. 9 illustrates the inhibition of growth of ERG harboring colon cancer cells (COLO320) by Compounds 1 and 2 at concentrations of 0.25 μM and 1 μM.
Figure 9:
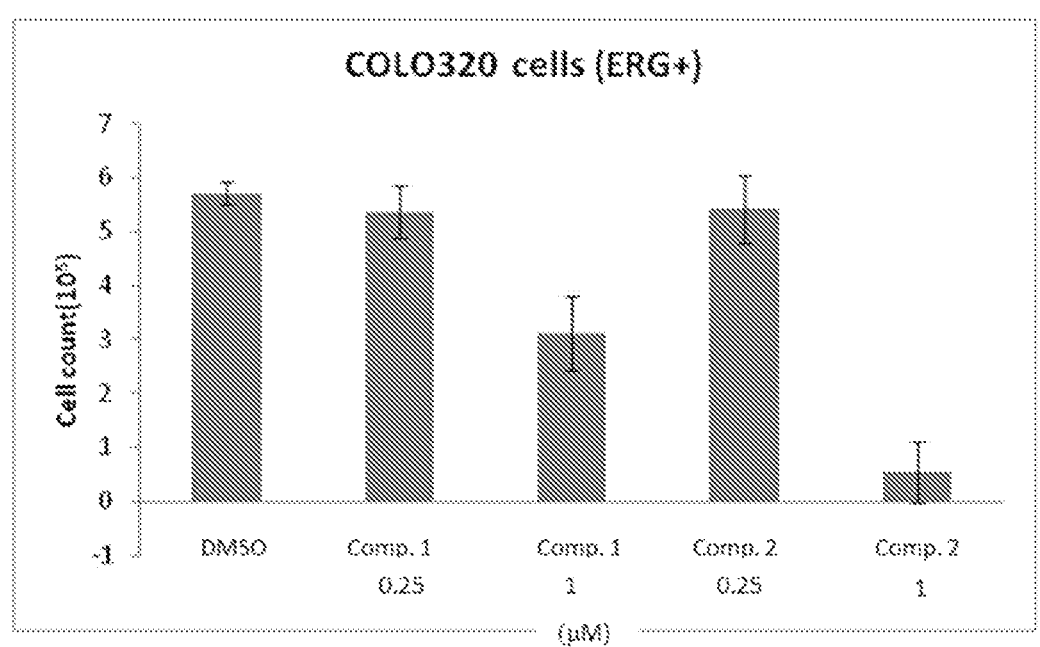
Figure 10:
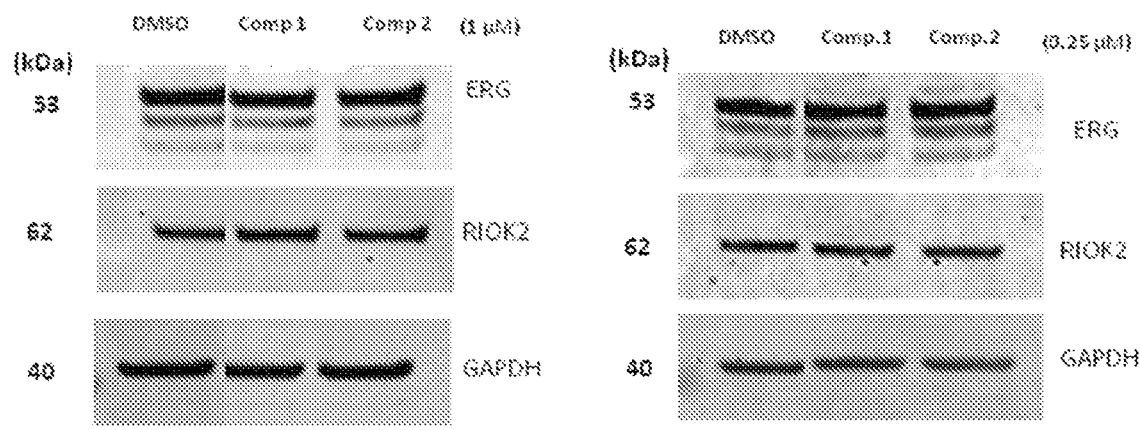
FIG. 10 illustrates the lack of inhibition of ERG and RIOK2 proteins in endogenous ERG expressing normal endothelial cells (HUVEC) by Compounds 1 and 2 at concentrations of 0.25 μM and 1 μM.
Figure 10:
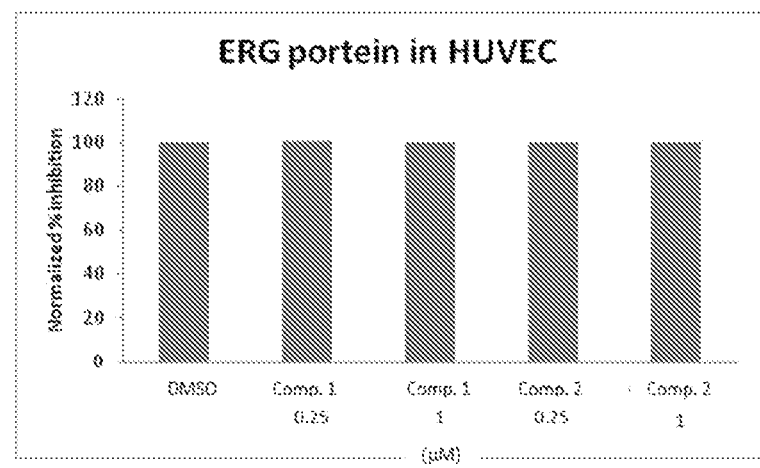
Figure 10:
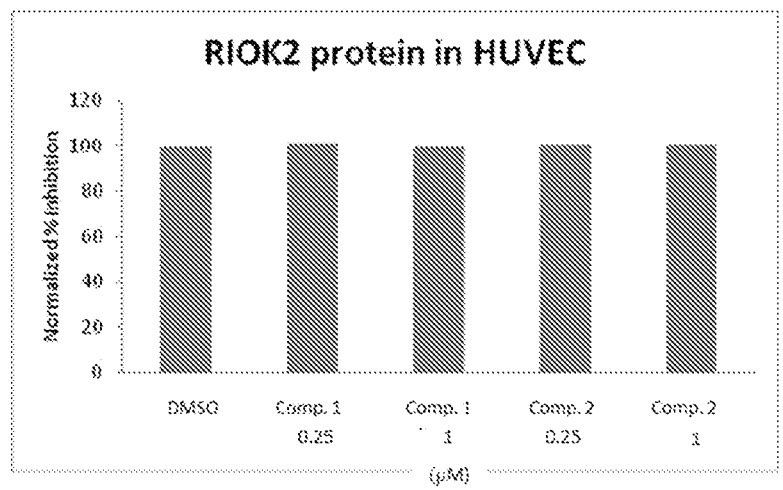
Figure 11:
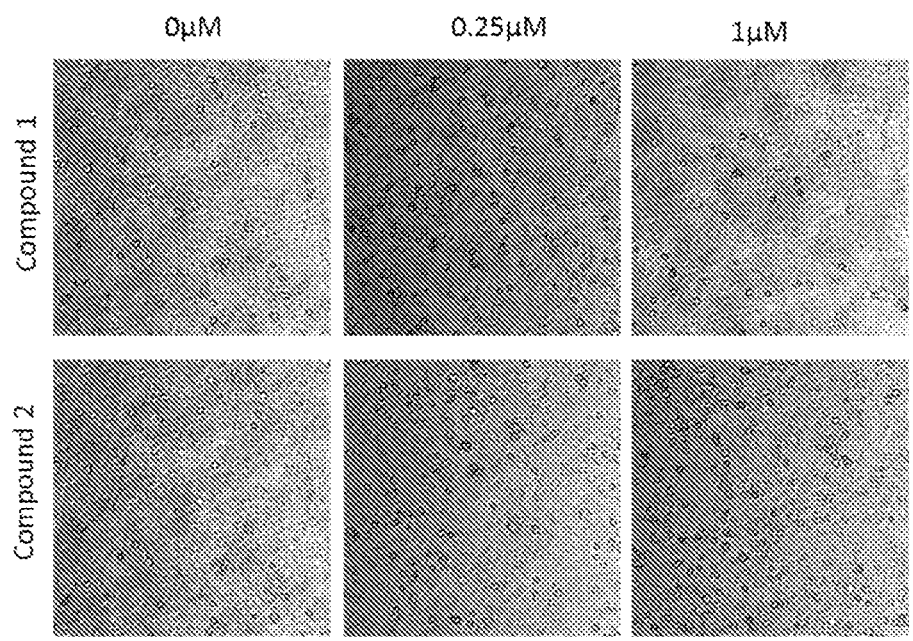
FIG. 11 illustrates that Compounds 1 and 2 at concentrations of 0.25 μM and 1 μM do not affect the growth of ERG harboring normal endothelial cells (HUVEC).
Figure 11:
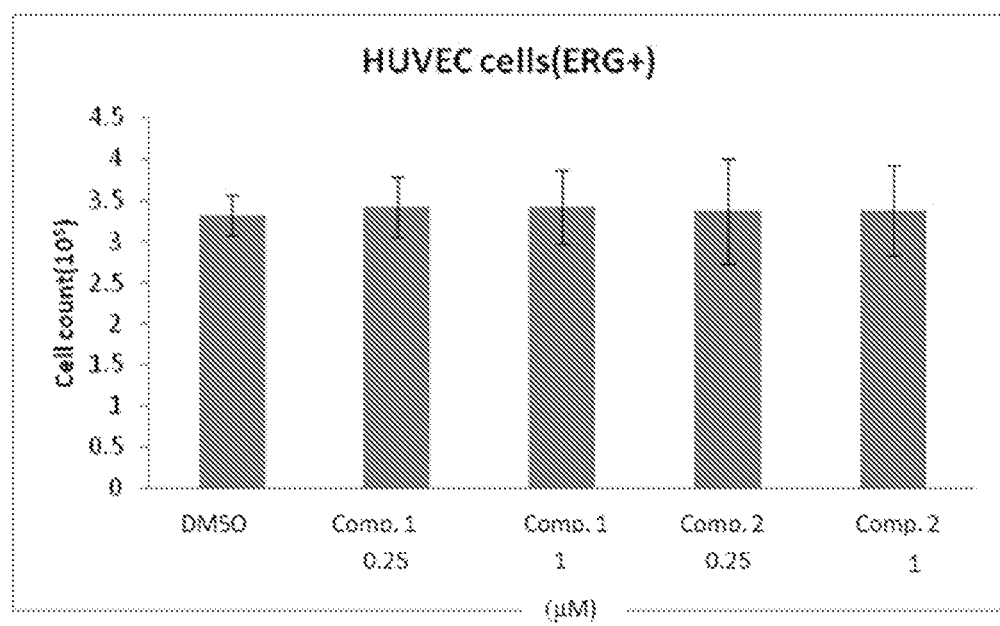
Figure 12:
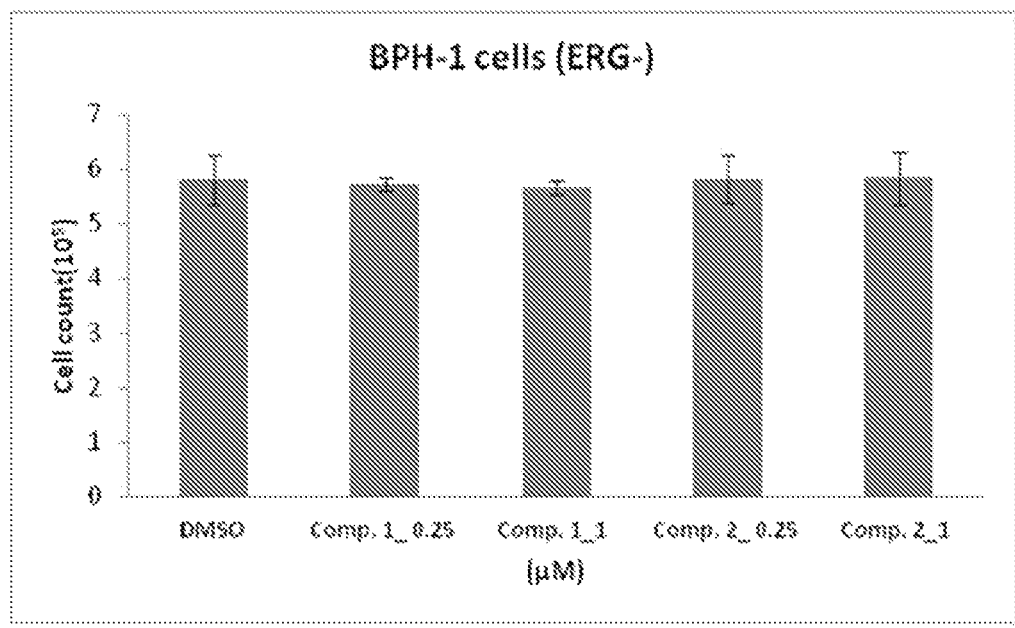
FIG. 12 illustrates that Compounds 1 and 2 at concentrations of 0.25 μM and 1 μM do not affect the growth of ERG negative prostate-derived immortalized cells (BPH-1 and RWPE-1).
Figure 12:
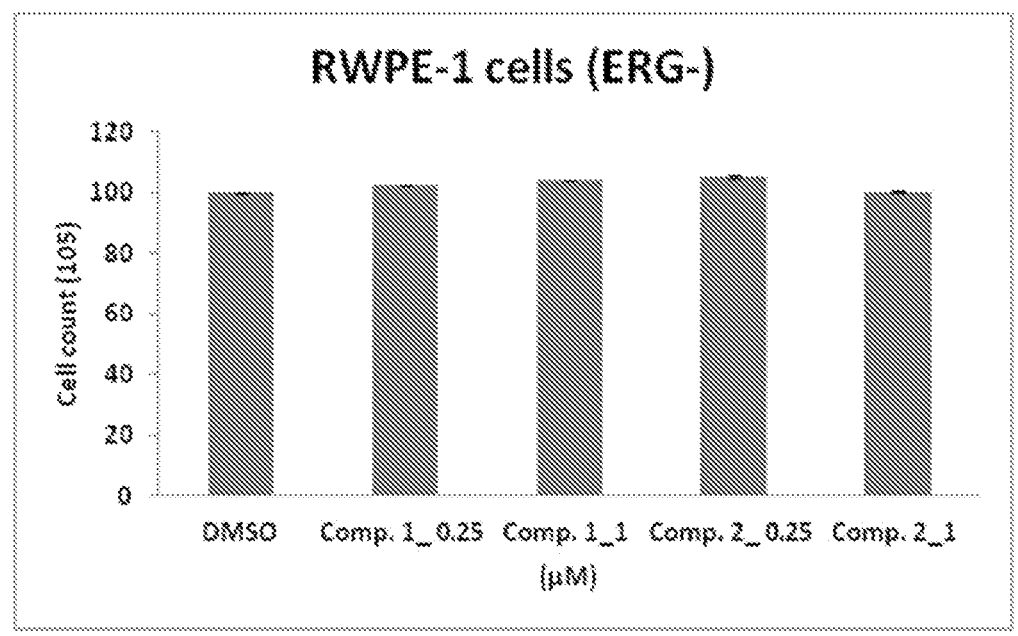
Figure 13:
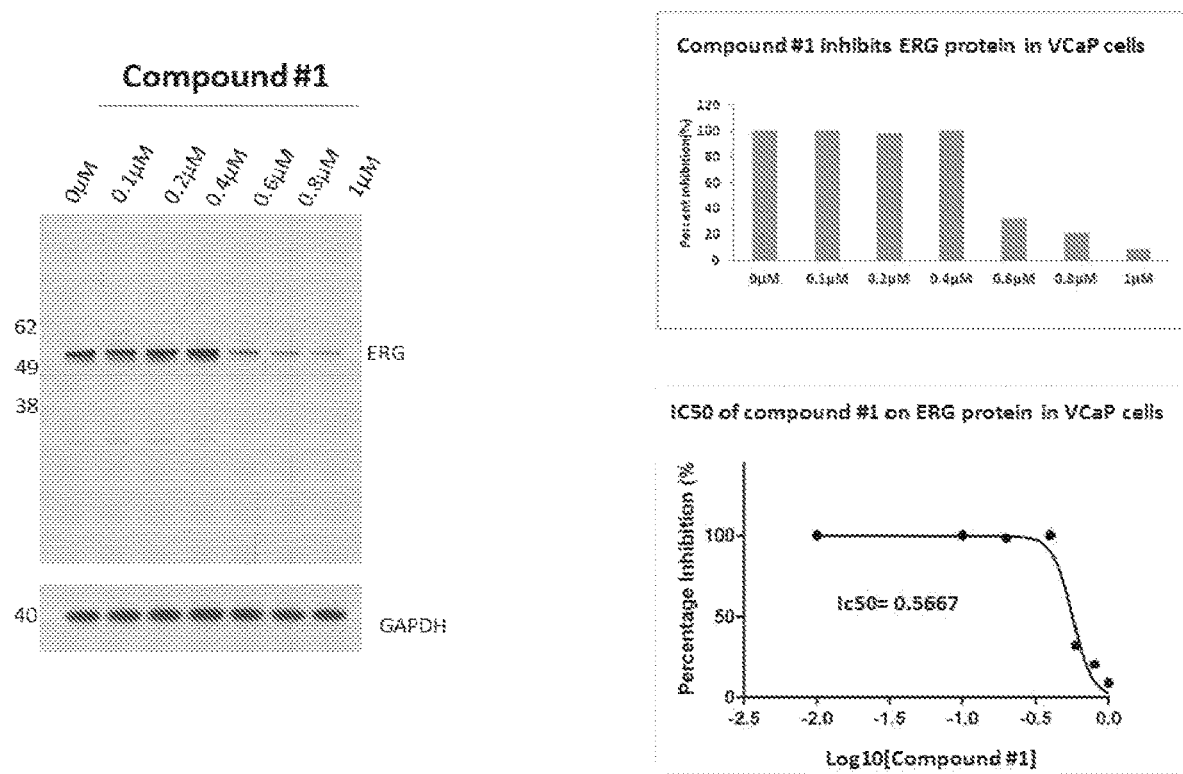
FIG. 13 illustrates the inhibition of ERG protein in VCaP cells by Compound 1 at concentrations of 0.1 μM, 0.2 μM, 0.4 μM, 0.6 μM, 0.8 μM and 1 μM and shows the $IC_{50}$ of Compound 1 on ERG protein in VCaP.
Figure 14:
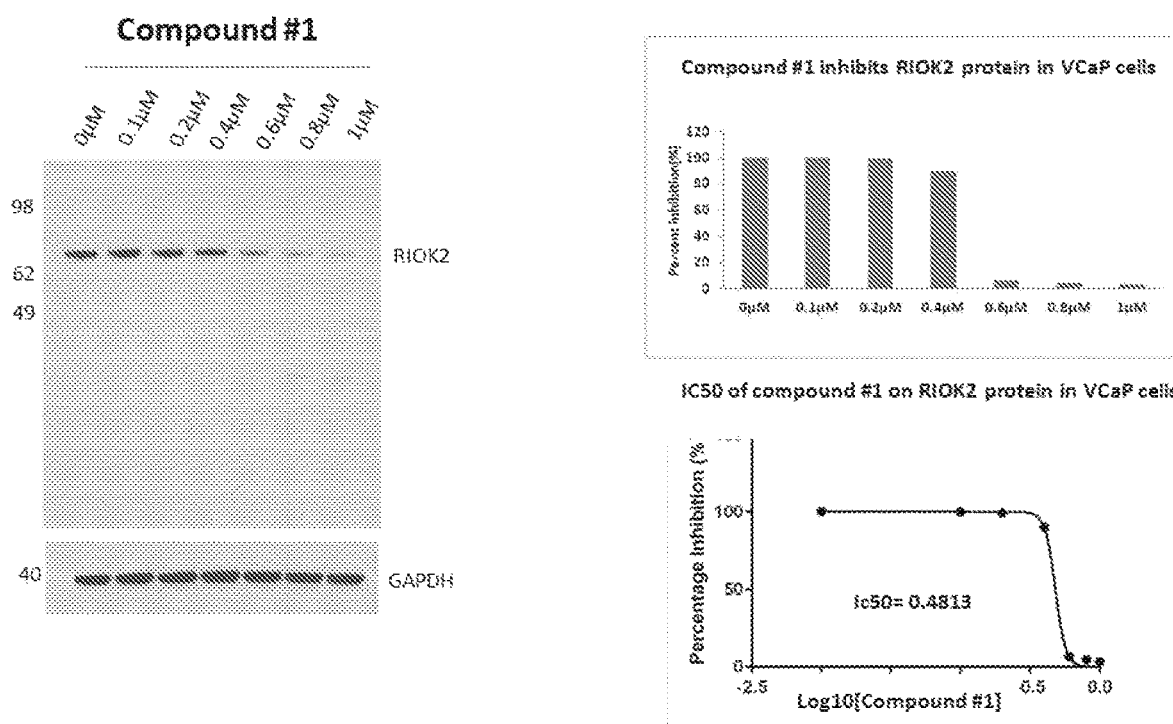
FIG. 14 illustrates the inhibition of RIOK2 protein in VCaP cells by Compound 1 at concentrations of 0.1 μM, 0.2 μM, 0.4 μM, 0.6 μM, 0.8 μM and 1 μM and shows the $IC_{50}$ of Compound 1 on RIOK2 protein in VCaP.
Figure 15:
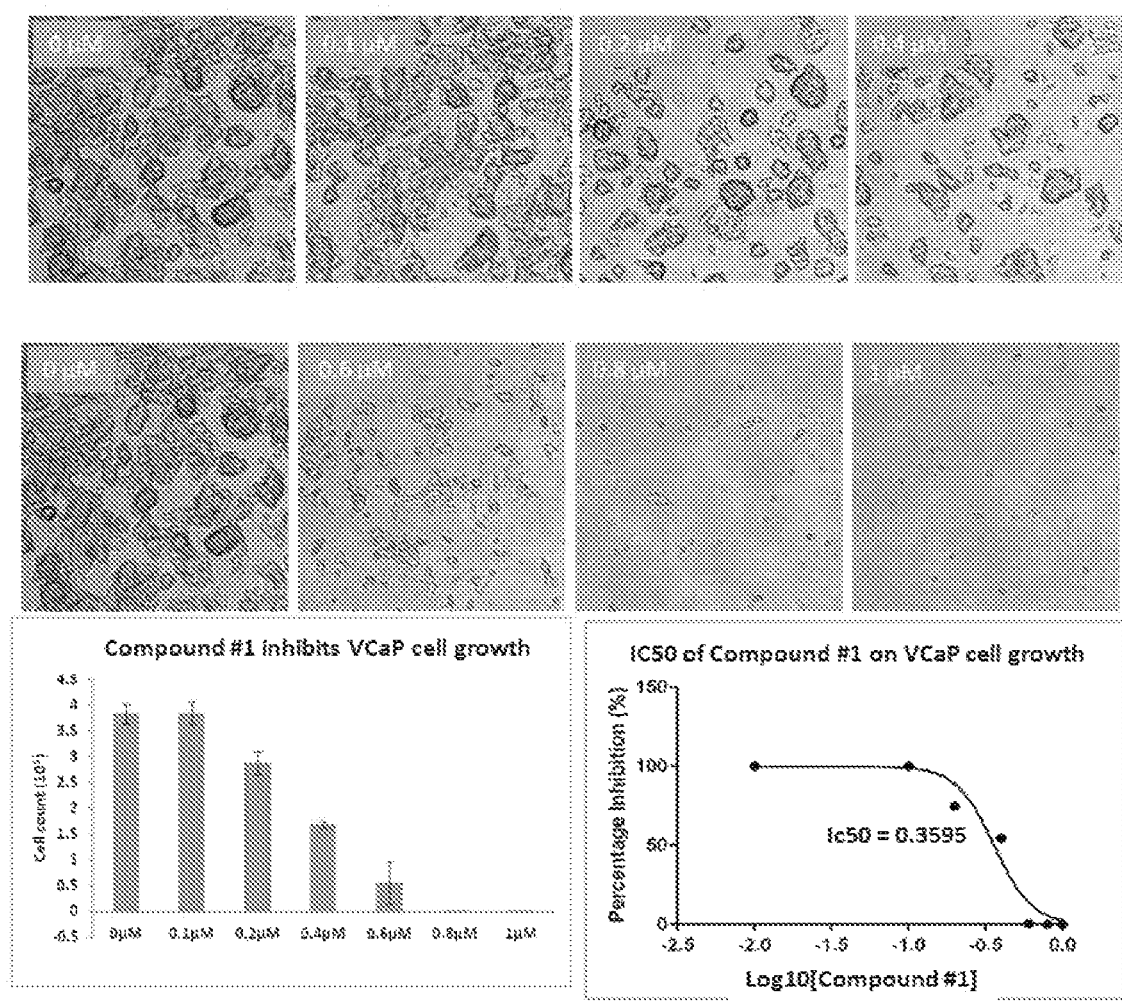
FIG. 15 illustrates the inhibition of VCaP cell growth by Compound 1 at concentrations of 0.1 μM, 0.2 μM, 0.4 μM, 0.6 μM, 0.8 μM and 1 μM.
Figure 16:
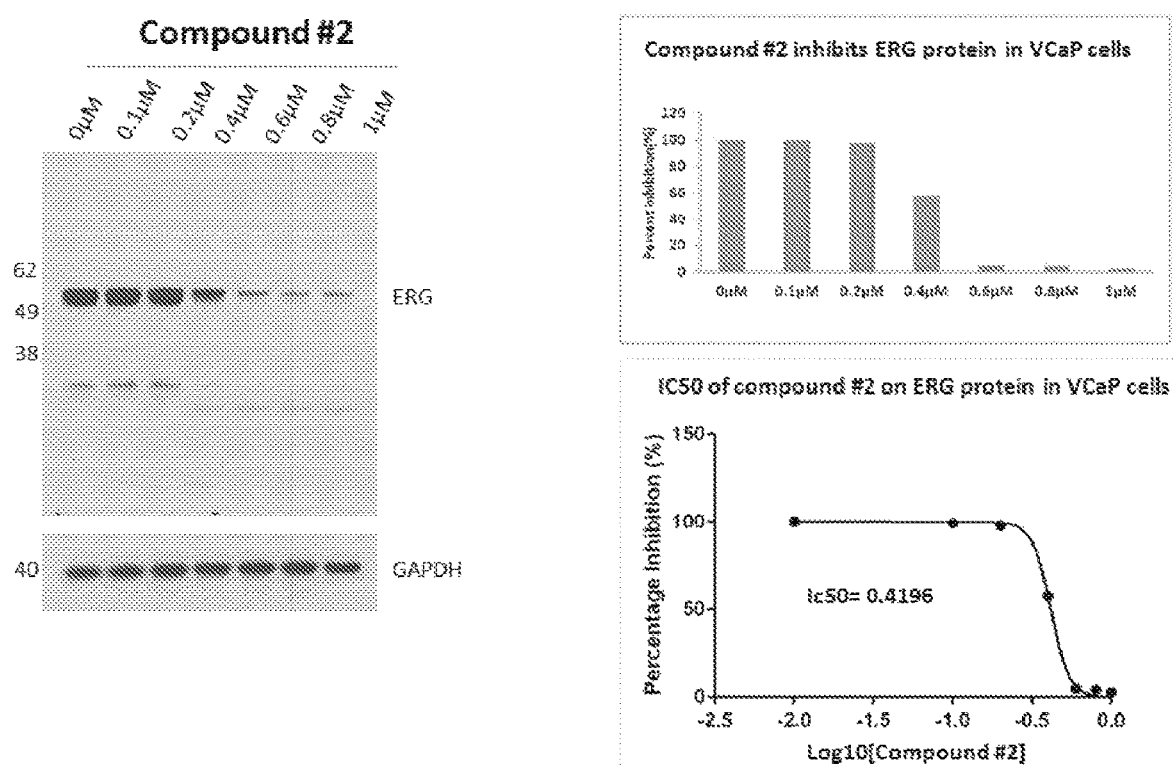
FIG. 16 illustrates the inhibition of ERG protein in VCaP cells by Compound 2 at concentrations of 0.1 μM, 0.2 μM, 0.4 μM, 0.6 μM, 0.8 μM and 1 μM and shows the $IC_{50}$ of Compound 2 on ERG protein in VCaP.
Figure 17:
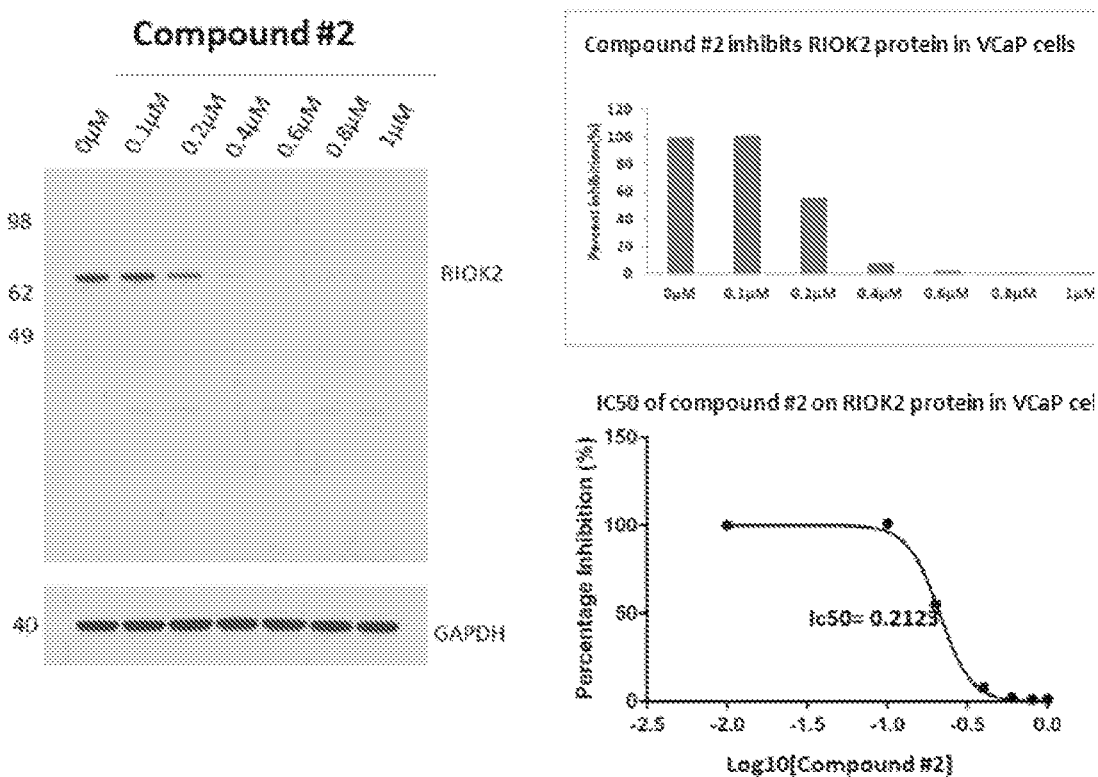
FIG. 17 illustrates the inhibition of RIOK2 protein in VCaP cells by Compound 2 at concentrations of 0.1 μM, 0.2 μM, 0.4 μM, 0.6 μM, 0.8 μM and 1 μM and shows the $IC_{50}$ of Compound 2 on RIOK2 protein in VCaP.
Figure 18:
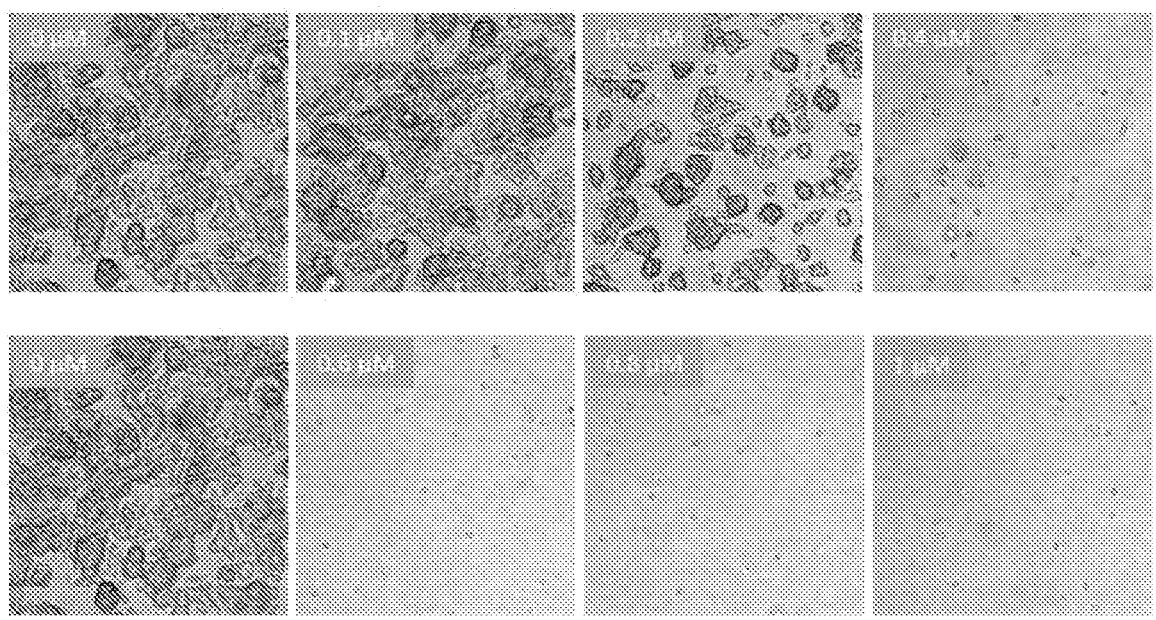
FIG. 18 illustrates the inhibition of VCaP cell growth by Compound 2 at concentrations of 0.1 μM, 0.2 μM, 0.4 μM, 0.6 μM, 0.8 μM and 1 μM.
Figure 18:
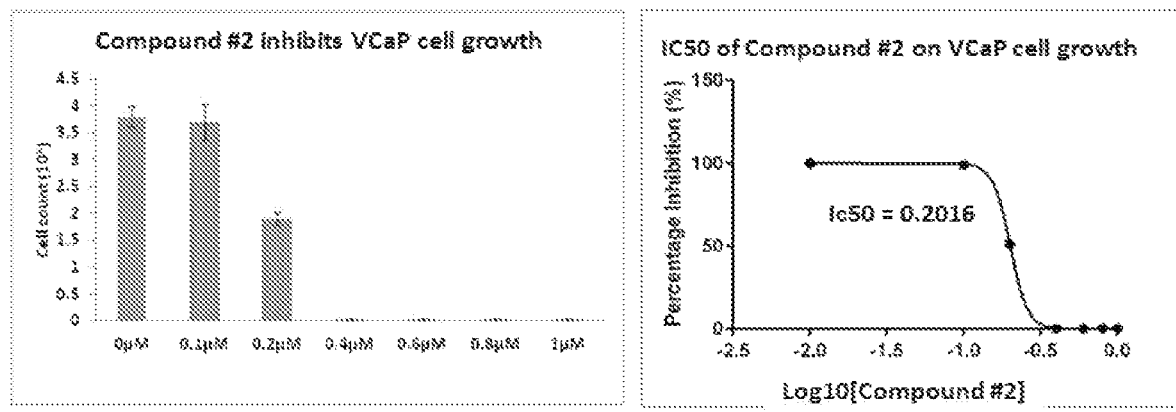
Figure 19:
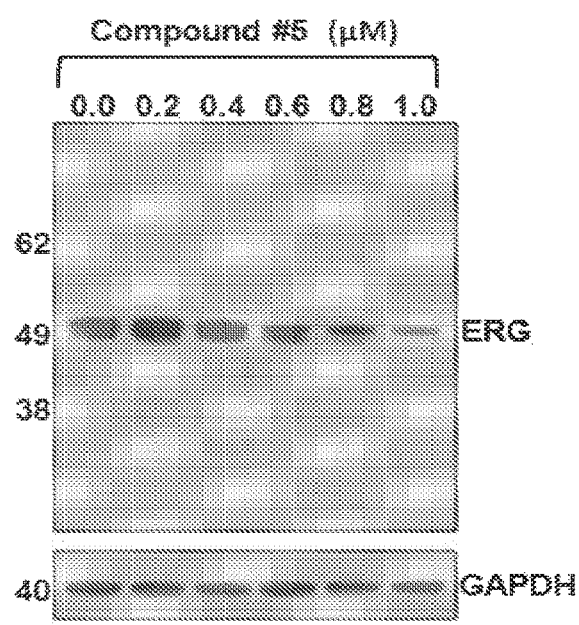
FIG. 19 illustrates the inhibition of VCaP cell growth by Compound 5 at concentrations of 0.2 μM, 0.4 μM, 0.6 μM, 0.8 μM and 1 μM and shows the $IC_{50}$ of Compound 5 on ERG protein in VCaP.
Figure 19:
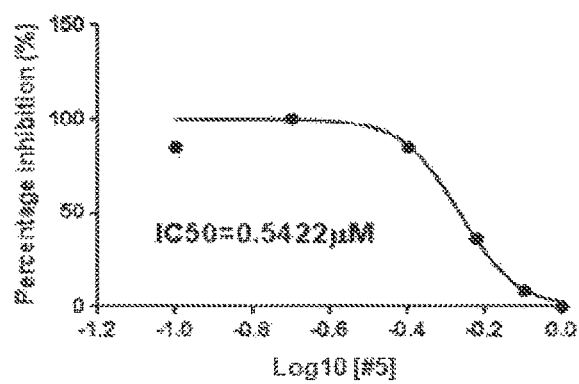
Figure 20:
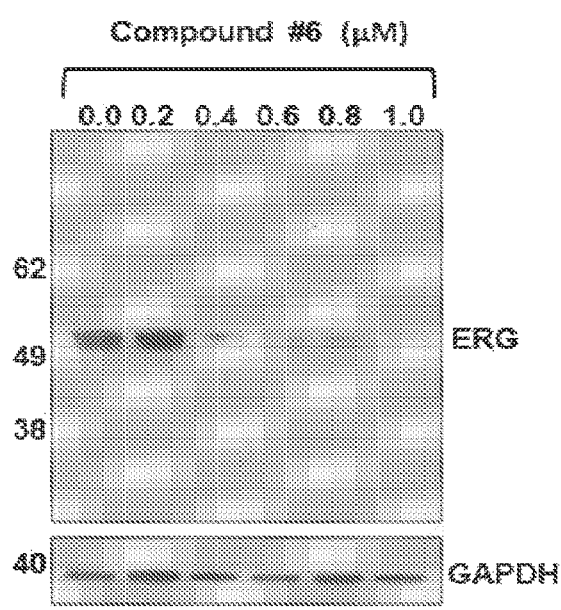
FIG. 20 illustrates the inhibition of VCaP cell growth by Compound 6 at concentrations of 0.2 μM, 0.4 μM, 0.6 μM, 0.8 μM and 1 μM and shows the $IC_{50}$ of Compound 6 on ERG protein in VCaP.
Figure 20:
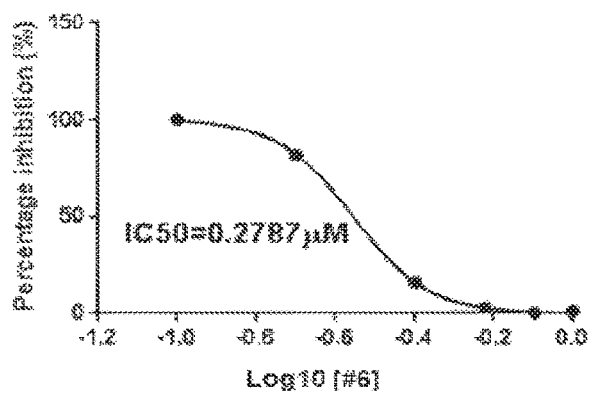
Figure 21:
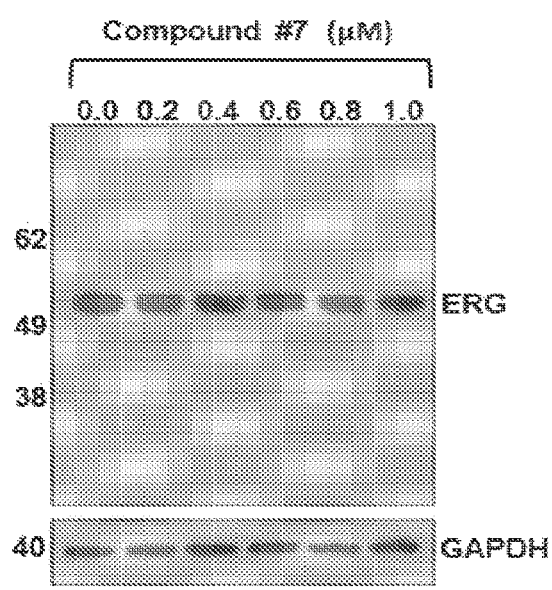
FIG. 21 illustrates the inhibition of VCaP cell growth by Compound 7 at concentrations of 0.2 μM, 0.4 μM, 0.6 μM, 0.8 μM and 1 μM and shows the $IC_{50}$ of Compound 7 on ERG protein in VCaP.
Figure 21:
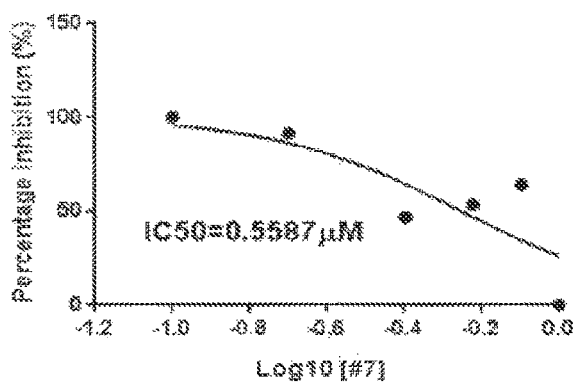
Figure 22:
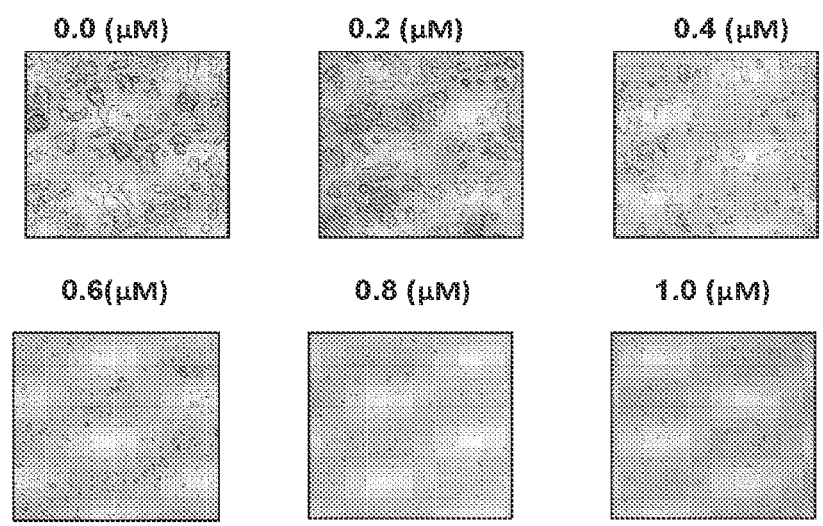
FIG. 22 illustrates the inhibition of VCaP cell growth by Compound 5 at concentrations of 0.2 μM, 0.4 μM, 0.6 μM, 0.8 μM and 1 μM and shows the IC50 of Compound 5 on cell growth.
Figure 22:
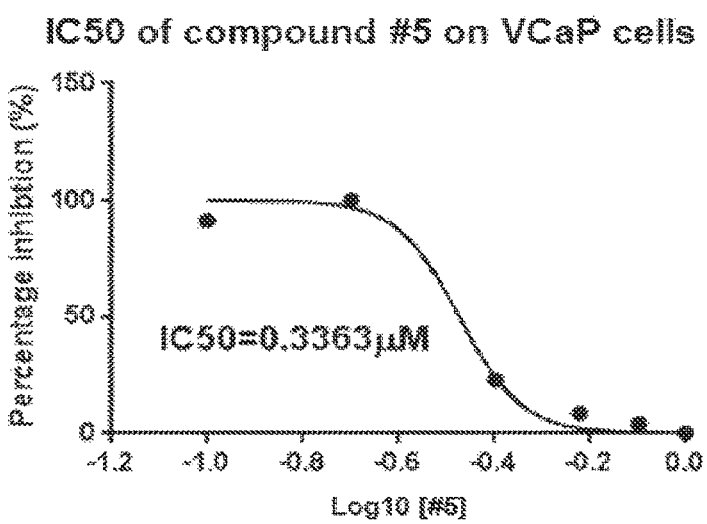
Figure 23:
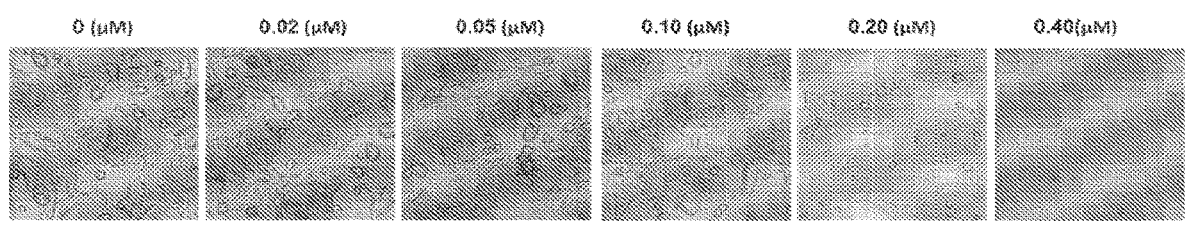
FIG. 23 illustrates the inhibition of VCaP cell growth by Compound 6 at concentrations of 0.02 μM, 0.05 μM, 0.10 μM, 0.20 μM and 0.40 μM and shows the IC50 of Compound 6 on cell growth.
Figure 23:
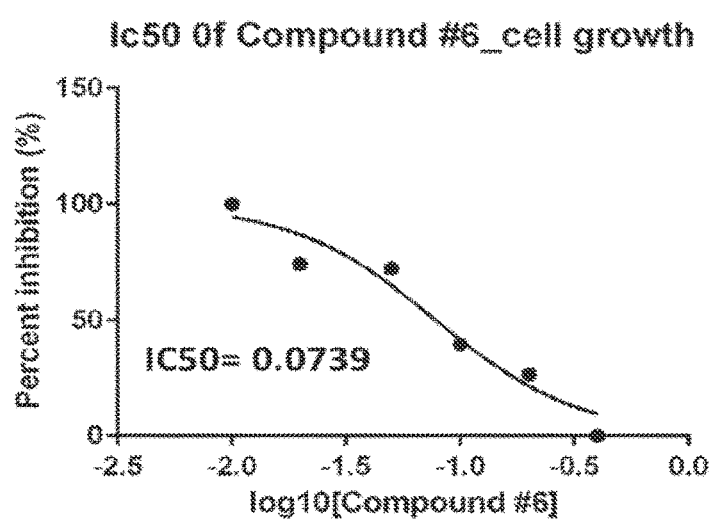
Figure 24:
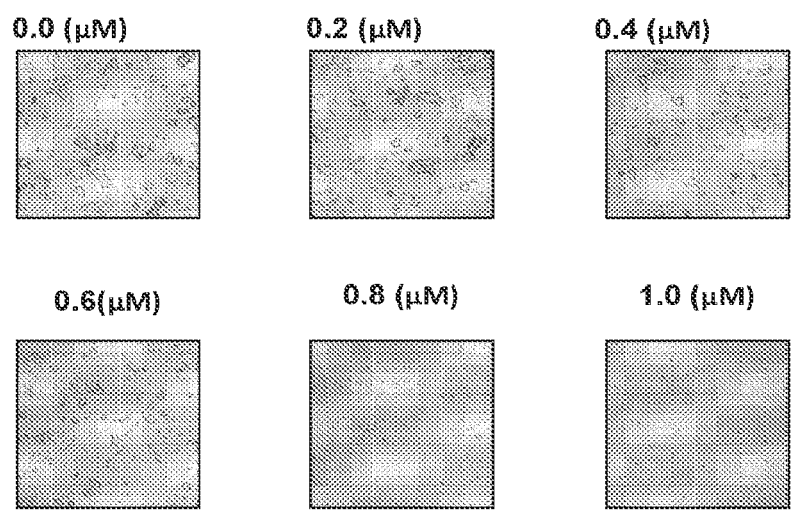
FIG. 24 illustrates the inhibition of VCaP cell growth by Compound 7 at concentrations of 0.2 μM, 0.4 μM, 0.6 μM, 0.8 μM and 1 μM and shows the $IC_{50}$ of Compound 7 on cell growth.
Figure 24:
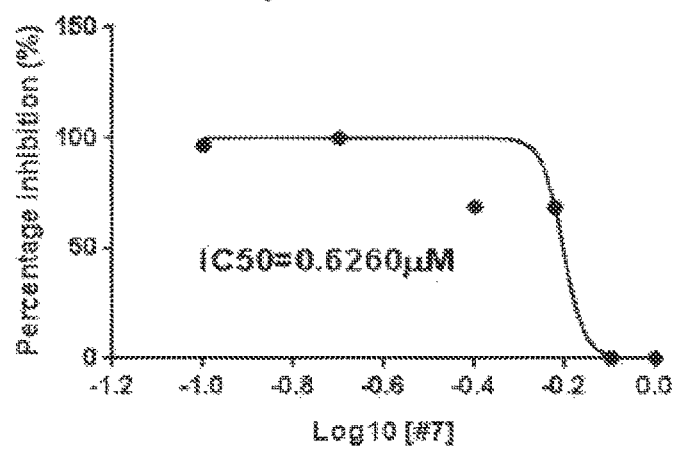
Figure 25:
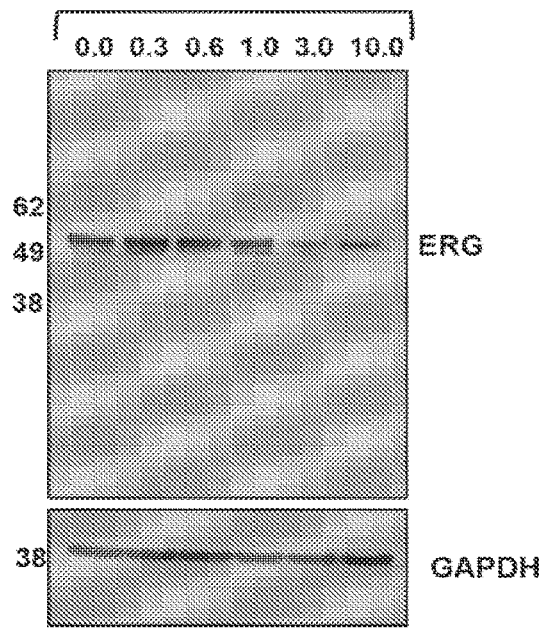
FIG. 25 illustrates the inhibition of VCaP cell growth by Compound 3 at concentrations of 0.3 μM, 0.6 μM, 1.0 μM, 3.0 μM and 10.0 μM and shows the $IC_{50}$ of Compound 3 on ERG protein in VCaP.
Figure 25:
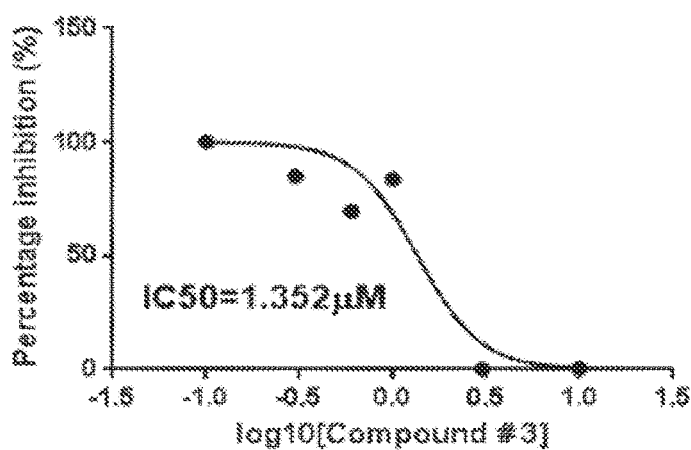
Figure 26:
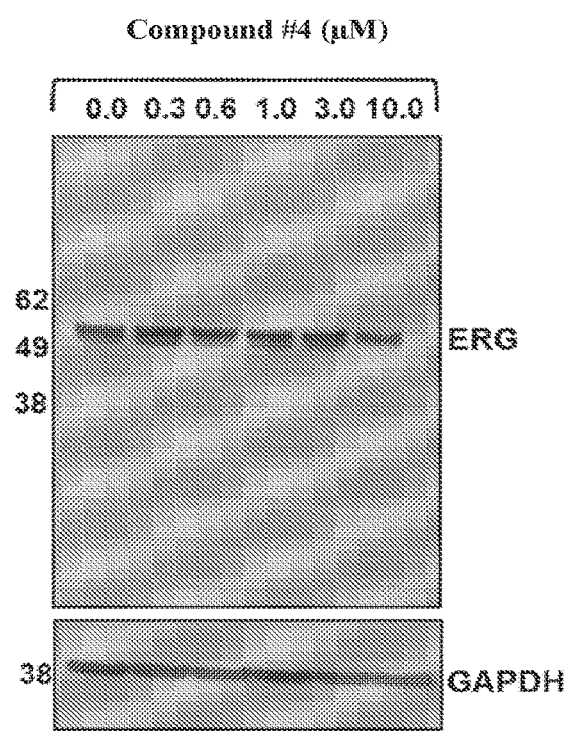
FIG. 26 illustrates the inhibition of VCaP cell growth by Compound 4 at concentrations of 0.3 μM, 0.6 μM, 1.0 μM, 3.0 μM and 10.0 μM and shows the $IC_{50}$ of Compound 4 on ERG protein in VCaP.
Figure 26:
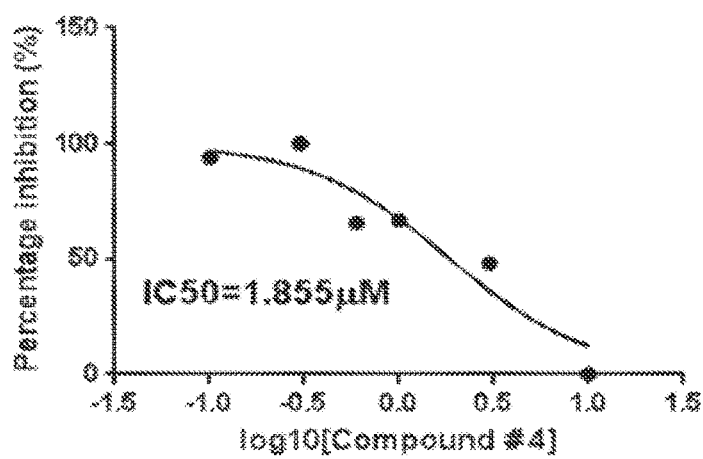
Figure 27:
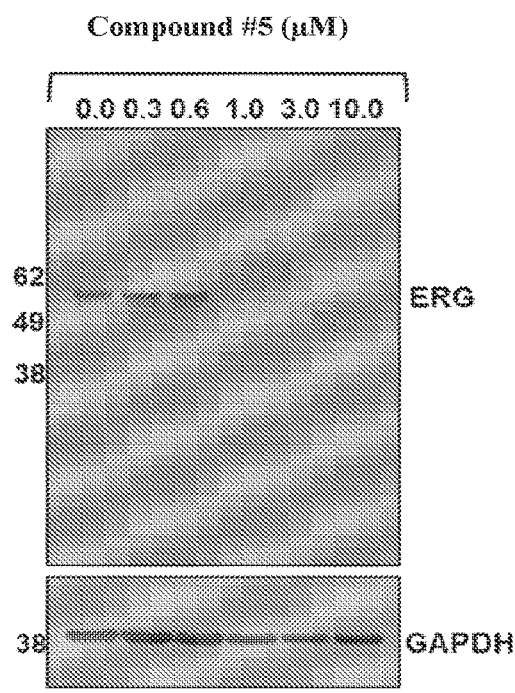
FIG. 27 illustrates the inhibition of VCaP cell growth by Compound 5 at concentrations of 0.3 μM, 0.6 μM, 1.0 μM, 3.0 μM and 10.0 μM and shows the $IC_{50}$ of Compound 5 on ERG protein in VCaP.
Figure 27:
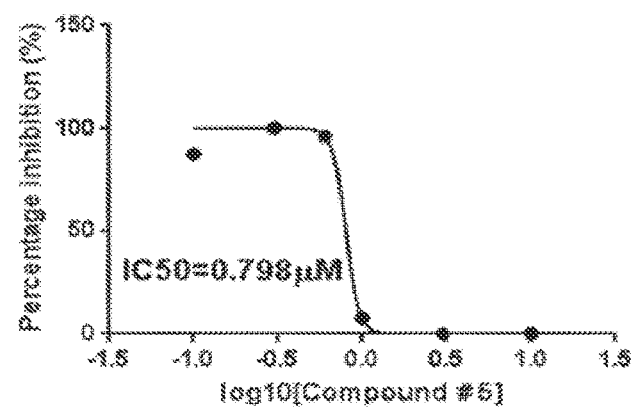
Figure 28:
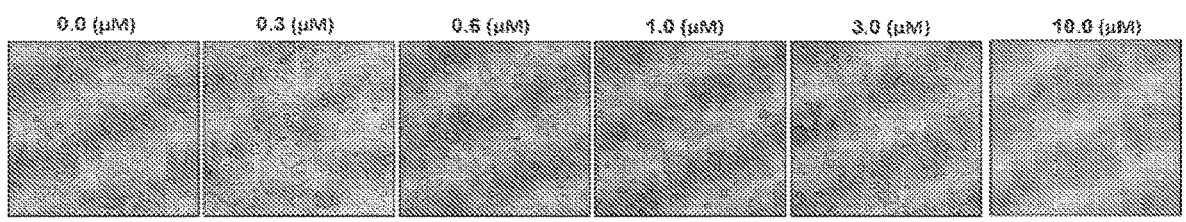
FIG. 28 illustrates the inhibition of VCaP cell growth by Compound 3 at concentrations of 0.3 μM, 0.6 μM, 1.0 μM, 3.0 μM and 10.0 μM and shows the $IC_{50}$ of Compound 3 on VCaP cell growth.
Figure 28:
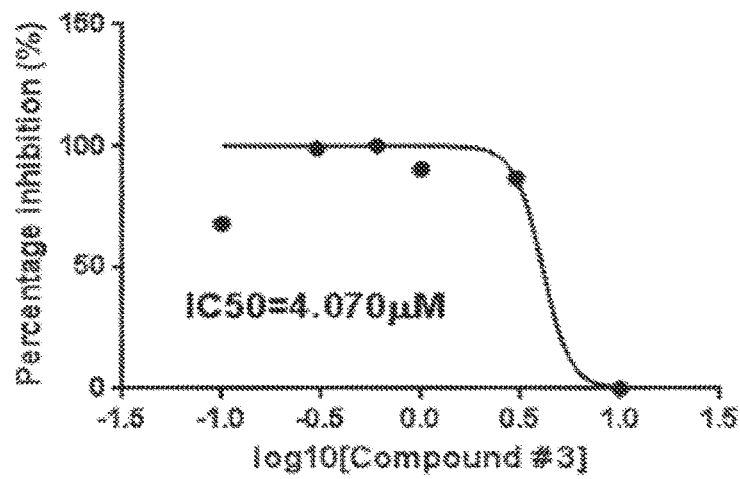
Figure 29:
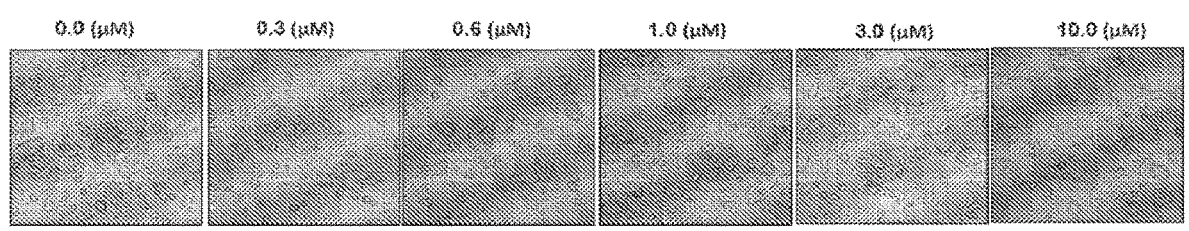
FIG. 29 illustrates the inhibition of VCaP cell growth by Compound 4 at concentrations of 0.3 μM, 0.6 μM, 1.0 μM, 3.0 μM and 10.0 μM and shows the $IC_{50}$ of Compound 4 on VCaP cell growth.
Figure 29:
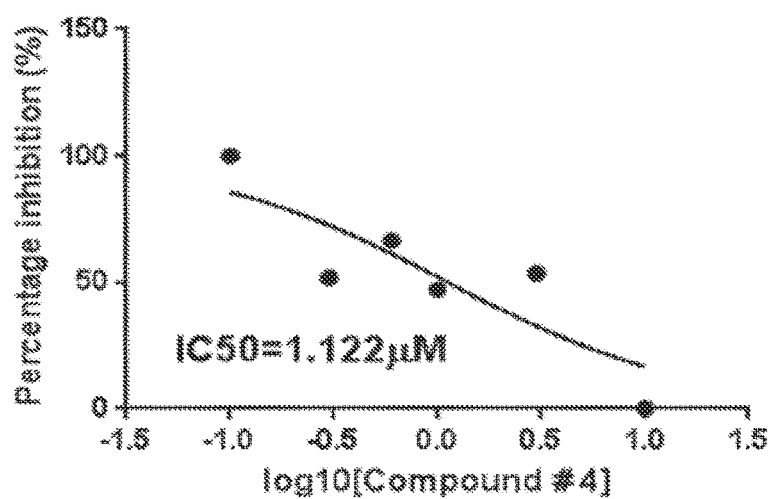
Figure 30:
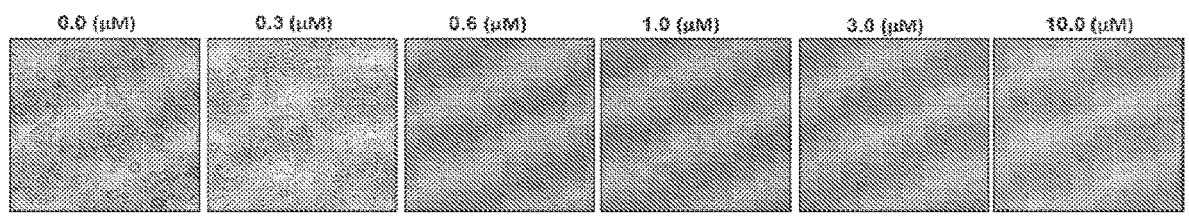
FIG. 30 illustrates the inhibition of VCaP cell growth by Compound 5 at concentrations of 0.3 μM, 0.6 μM, 1.0 μM, 3.0 μM and 10.0 μM and shows the $IC_{50}$ of Compound 5 on VCaP cell growth.
Figure 30:
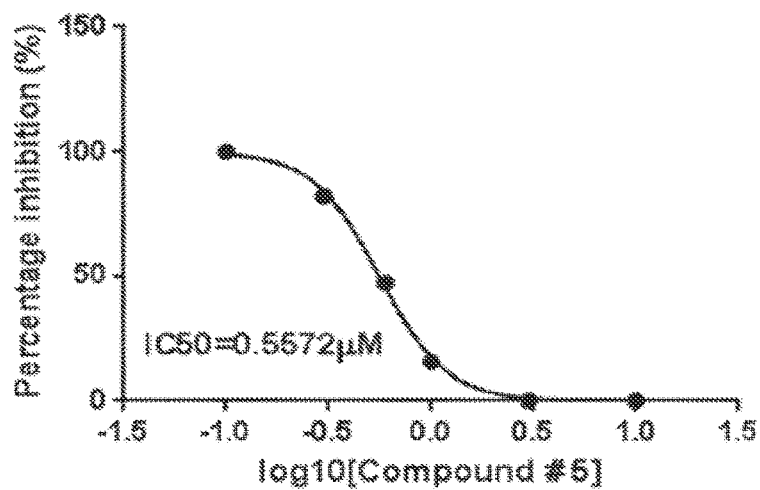

A "pharmaceutically acceptable salt" is a pharmaceutically acceptable, organic or inorganic acid or base salt of a compound of the invention. Representative pharmaceutically acceptable salts include, e.g., alkaline metal salts, alkaline earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions.

Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the invention, or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

A "subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a subject is a human, such as a human infant, child, adolescent or adult.

The term "substituted", as used herein, refers to the replacement of at least one hydrogen atom of a molecular arrangement with a substituent. In the case of an oxo substituent ("=O"), two hydrogen atoms are replaced. When substituted, one or more of the groups below are "substituents." Substituents include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocyclyl, and heterocycloalkyl; —NRaRb, —NRaC(O)Rb, —NRaC(O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)ORa. In addition, the above substituents may be further substituted with one or more of the above substituents, such that the substituent comprises a substituted alkyl, substituted aryl, substituted arylalkyl, substituted heterocycle, or substituted heterocycloalkyl. Ra and Rb in this context may be the same or different and, independently, hydrogen, alkyl, haloalkyl, substituted alkyl, aryl, substituted aryl, arylalkyl, substituted arylalkyl, heterocyclyl, substituted heterocyclyl, heterocycloalkyl or substituted heterocycloalkyl.

The term "unsubstituted", as used herein, refers to any compound that does not contain extra substituents attached to the compound. An unsubstituted compound refers to the chemical makeup of the compound without extra substituents, e.g., the compound does not contain protecting group(s). For example, unsubstituted proline is a proline amino acid even though the amino group of proline may be considered disubstituted with alkyl groups.

The term "alkyl", as used herein, refers to any straight chain or branched, non-cyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 7 to 10 carbon atoms. Representative saturated straight chain alkyls include, but are not limited to, methyl, ethyl, n-propyl, n-butyl, n-pentyl, n-hexyl, n-heptyl, n-octyl, n-nonyl, and the like; while saturated branched alkyls include, but are not limited to, isopropyl, sec-butyl, isobutyl, tert-butyl, isopentyl, and the like. Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl", as used herein, refers to any aromatic carbocyclic moiety such as, but not limited to, phenyl or naphthyl.

The term "arylalkyl", or "aralkyl" as used herein, refers to any alkyl having at least one alkyl hydrogen atom replaced with an aryl moiety, such as, but not limited to, benzyl, —(CH$_2$)$_2$-phenyl, —(CH$_2$)$_3$-phenyl, —CH(phenyl)$_2$, and the like.

The term "halogen", as used herein, refers to any fluoro, chloro, bromo, or iodo moiety.

The term "haloalkyl", as used herein, refers to any alkyl having at least one hydrogen atom replaced with halogen, such as trifluoromethyl, and the like.

The term "heteroaryl", as used herein, refers to any aromatic heterocycle ring of 5 to 10 members and having at least one heteroatom selected from nitrogen, oxygen and sulfur, and containing at least 1 carbon atom, including, but not limited to, both mono and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, or quinazolinyl.

The term "heteroarylalkyl", as used herein, refers to any alkyl having at least one alkyl hydrogen atom replaced with a heteroaryl moiety, such as —CHpyridinyl, —CH$_2$pyrimidinyl, and the like.

The term "heterocycle" or "heterocyclic ring", as used herein, refers to any 3- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles may include heteroaryls exemplified by those defined above. Thus, in addition to the heteroaryls listed above, heterocycles may also include, but are not limited to, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

The term "heterocycloalkyl", as used herein, refers to any alkyl having at least one alkyl hydrogen atom replaced with a heterocycle, such as —CH$_2$-morpholinyl, and the like.

The term "homocycle" or "cycloalkyl", as used herein, refers to any saturated or unsaturated (but not aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino", as used herein, refers to at least one alkyl moiety attached through a nitrogen bridge (e.g., —N-alkyl or —N-(alkyl)-N—) including, but not limited to, methylamino, ethylamino, dimethylamino, diethylamino, and the like.

The term "alkyloxy" or "alkoxy", as used herein, refers to any alkyl moiety attached through an oxygen bridge (e.g., —O-alkyl) such as, but not limited to, methoxy, ethoxy, and the like.

The term "alkylthio", as used herein, refers to any alkyl moiety attached through a sulfur bridge (e.g., —S-alkyl) such as, but not limited to, methylthio, ethylthio, and the like.

The term "alkenyl" refers to an unbranched or branched hydrocarbon chain having one or more double bonds therein. The double bond of an alkenyl group can be unconjugated or conjugated to another unsaturated group. Suitable alkenyl groups include, but are not limited to vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkynyl" refers to unbranched or branched hydrocarbon chain having one or more triple bonds therein. The triple bond of an alkynyl group can be unconjugated or conjugated to another unsaturated group. Suitable alkynyl groups include, but are not limited to ethynyl, propynyl, butynyl, pentynyl, hexynyl, methylpropynyl, 4-methyl-1-butynyl, 4-propyl-2-pentynyl-, and 4-butyl-2-hexynyl. An alkynyl group can be unsubstituted or substituted with one or two suitable substituents.

Compounds and Methods

The present invention relates to selective azophenol ERG inhibitor compounds and to their use for treating or preventing a disease related to over-expression of an ETS Related Gene (ERG), a wild type ERG protein or an altered ERG protein in a subject. More specifically, the azophenol ERG inhibitors of the invention do not attenuate or inhibit androgen receptor (AR) signaling in ERG negative AR positive CaP cell lines tested and thus exhibit fewer toxic side effects when compared to conventional agents that inhibit AR signaling as the underlying mechanism for treating prostate cancer. Additionally, the azophenols of the invention inhibit ERG protein, and cell growth in the ERG positive tumor cell lines that do not express AR.

Approved strategies for the treatment of prostate cancer routinely entail therapeutic agents that attenuate or inhibit the activity of AR in prostate cancer cells. Because the expression of ERG in VCaP prostate cancer cells is regulated by AR, representative azophenol compounds of the invention were evaluated to determine if the observed ERG inhibitory activity was a result of AR inhibition. The azophenol compounds were observed to inhibit the expression of AR and prostate specific antigen (PSA) in VCaP prostate cancer cells.

To investigate whether the azophenol compounds of the invention are selective inhibitors of ERG protein expression, representative azophenol compounds were further tested for its ability to inhibit AR and PSA activity in the following AR positive/ERG negative prostate cancer cell lines: LNCaP (mutant AR positive and ERG negative), as well as in LAPC4 cells that are AR (wild type) positive and ERG negative.

Inhibition of AR by a representative azophenol compound of the invention is specific to VCaP cells. No AR inhibition was observed in other AR positive/ERG negative cell lines used in this screen.

In an exemplary embodiment, a method for treating or preventing a disease related to overexpression of wild type ERG protein or an altered ERG protein product of the E-Related Gene (ERG) in a subject by administering to the subject a therapeutically-effective amount of an azophenol compound of the invention that selectively inhibits ERG expression. While the exact mechanism by which ERG expression is lowered or inhibited is unknown, the azophenol compounds may, for example, influence ERG mRNA gene transcription, ERG mRNA translation, prevent ERG protein from attaining its functionally active tertiary structure or inhibit the growth of ERG positive tumors by altering the regulation of a gene that is essential for cell growth.

The azophenol compounds of the invention appear to selectively inhibit ERG expression in cancer cells without inhibiting the expression of ERG in normal endothelial cells. A representative azophenol compound of the invention inhibits expression of ERG in a dose dependent manner in ERG positive cancer cell lines. No measurable inhibition of ERG protein expression was observed in normal HUVEC cells, with basal expression of ERG, however.

ERG overexpression in cancer cells is believed to play a role in the development of oncogene addiction, a condition in which some ERG positive cancer cells depend on the activity of the ERG protein for their growth and survival. Inhibition or attenuation of ERG protein expression in ERG positive cancer cells, therefore, may arrest the growth and survival of cancer cells. As illustrated by the results of a cell growth inhibition study, inhibition of ERG expression prevents growth of ERG positive cancer cells. No cell growth inhibition effects were observed, however, for ERG negative prostate cancer cell lines, an ERG negative immortalized benign prostate cell line (BPH1), and for ERG positive normal cells. These results support the use of the azophenol compounds of the invention as candidate therapeutic agents for the selective treatment of ERG positive cancers, such as, for example, prostate cancer. In an exemplary embodiment, methods for treating ERG positive cancers using the azophenol compounds of the invention therefore provide an unexpected approach for treating metastatic hormone refractory prostate cancer that is unresponsive to treatment with agents that attenuate or inhibit AR activity and/or ablate hormonal activity.

The azophenol inhibitors of ERG overexpression according to the invention may also be used in combination with one or more other therapeutic agents capable of treating cancers. In an exemplary embodiment, the azophenol compounds are used in combination with conventional inhibitors of AR activity for the treatment of prostate cancer, particularly for subject diagnosed with prostate cancer, in which the AR activity is amplified or super activated.

The azophenol compounds of the invention were further evaluated as a candidate therapeutic agent for treating a patient having an ERG positive cancer. Separate cultures of ERG positive VCaP prostate cancer cells and ERG negative LNCaP cells were used to test for selective inhibition of ERG expression and the cell growth inhibitory activity of several representative azophenol compounds. The azophenol compounds of the invention are selective inhibitors of ERG expression and growth of ERG positive cancer cells.

The above observations and the role of ERG in cancer cell growth support the use of ERG specific inhibitors, such the azophenol compounds of the invention, as viable therapeutic agents for treating cancers such as prostate cancer, colorectal cancer, Ewing sarcoma, a vascular tumor and leukemia. In an exemplary embodiment, the subject receiving treatment for cancer according to a method of the invention is a mammal. For instance, the methods and uses described herein are suitable for the treatment of cancers in humans. Alternatively, the methods and uses of the invention may be suitable in a veterinary context, wherein the subject includes, but is not limited to, a dog, cat, horse or cow.

In select embodiments of the invention, the azophenol ERG inhibitors are co-administered with at least one anti-cancer therapeutic agent. As used herein, "co-administer" indicates that each of the at least two components is administered during a time frame wherein the respective periods of biological activity or effects overlap. Thus, the term "co-administer" is intended to encompass sequential as well as coextensive administration of the individual therapeutic components. Accordingly, "administering" the combination of components according to some of the methods of the present invention includes sequential as well as coextensive administration of the individual components of the present invention. Likewise, the phrase "combination of compounds" or "combination of components" and the like indicate that the individual components are coadministered, and these phrases do not necessarily mean that the compounds must be administered contemporaneously or coextensively. In addition, the routes of administration of the individual components need not be the same. In an exemplary embodiment, the azophenol compounds are administered in the same composition.

In an exemplary embodiment, at least one azophenol ERG inhibitor of the invention is co-administered with a prostate cancer therapy. In a more specific embodiment, the azophenol ERG inhibitors are co-administered with one or more of lutenizing hormone-releasing hormone (LHRH) analogs such as, but not limited to, leuprolide (Lupron®, Eligard®), goserelin (Zoladex®), triptorelin (Trelstar®), degarelix (Firmagon®), Abiraterone (Zytiga®) and histrelin (Vantas®). In other specific embodiments, the azophenol ERG inhibitors are co-administered with one or more of anti-androgen receptors such as, but not limited to, flutamide (Eulexin®), bicalutamide (Casodex®), Enzalutamide (Xandi®) and nilutamide (Nilandron®). In other specific embodiments, the azophenol ERG inhibitors are co-administered with one or more chemotherapeutics such as, but not limited to, Docetaxel (Taxotere®), Cabazitaxel (Jevtana®), Mitoxantrone (Novantrone®), Estramustine (Emcyt®). Doxorubicin (Adriamycin®), Etoposide (VP-16), Vinblastine (Velban®), Paclitaxel (Taxol®), Carboplatin (Paraplatin®), Vinorelbine (Navelbine®) Abiraterone (Zytiga), ARN-509 (J@J), and Galeterone (Tokai).

In an exemplary embodiment, the azophenol ERG inhibitors are administered as a first line therapy. In other embodiments, the azophenol ERG inhibitors are administered as a second line therapy or a third line therapy. In still other embodiments, the azophenol ERG inhibitors are administered subsequent to a third line therapy. As used herein, a first line therapy is the therapeutic regimen that is first prescribed or followed upon diagnosis of a condition that warrants the use of an ERG inhibitor, such as but not limited to prostate cancer. A second line therapy is the therapeutic regimen that is prescribed or followed upon diagnosis of a recurrence or metastasis of condition that warrants the use of an ERG inhibitor, such as but not limited to prostate cancer. Likewise, a third line therapy is the therapeutic regimen that is prescribed or followed upon diagnosis of a second recurrence or metastasis of condition that warrants the use of an ERG inhibitor, such as but not limited to prostate cancer. A therapy, for the purposes of determining which "line" of therapy as used herein, need not be a drug therapy. For example, a first line therapy, as used herein, may be surgical removal, or radiation therapy. Any therapy designed to remove, reduce or ablate the tumor or condition can be considered a "line" of therapy.

In other embodiments, the azophenol ERG inhibitors of the invention can be administered as a "maintenance" therapeutic. As used herein, a maintenance therapeutic is a therapeutic regimen that is prescribed or followed while the subject is free of any detectable condition requiring treatment, for example, after a tumor is surgically removed from the subject. In these embodiments, the ERG inhibitors can be taken, for example, after surgical resection, for a specified period of time such as, but not limited to, at least about six months, such as one year, two years, three years, four years or five years, after the removal or disappearance of the tumor or cancer.

Pharmaceutical Formulations, Routes of Administration and Dosing Regimen

Despite evidence generally associating ERG expression with cancer cell growth, the conventional art does not appear to consider a small molecule compound that selectively inhibits expression of ERG in cancer cells or the use of such selective ERG inhibitors as anti-neoplastic agents. The present invention provides azophenol compounds and their pharmaceutical compositions that are useful in treating a subject suffering from an ERG positive cancer, as more generally set forth above.

The azophenol compound or composition of the invention can be formulated as described herein and is suitable for administration in a therapeutically effective amount to the subject in any number of ways. A therapeutically effective amount of an azophenol compound as described herein depends upon the amounts and types of excipients used, the amounts and specific types of active ingredients in a dosage form, and the route by which the compound is to be administered to patients. However, typical dosage forms of the invention comprise a compound or a pharmaceutically acceptable salt of the compound.

Typical dosage levels for the azophenol compounds generally range from about 0.001 to about 100 mg per kg of the subject's body weight per day which can be administered in single or multiple doses. An exemplary dosage is about 0.01 to about 25 mg/kg per day or about 0.05 to about 10 mg/kg per day. In other exemplary embodiments, the dosage level ranges from about 0.01 to about 25 mg/kg per day, such as about 0.05 to about 10 mg/kg per day, or about 0.1 to about 5 mg/kg per day.

A dose can typically range from about 0.1 mg to about 2000 mg per day and can be given as a single once-a-day dose or, alternatively, as divided doses throughout the day, optionally taken with food. In a particular embodiment, the daily dose is administered twice daily in equally divided doses. A daily dose range can range from about 5 mg to about 500 mg per day such as, for example, between about 10 mg and about 300 mg per day. In managing the patient, the therapy can be initiated at a lower dose, such as from about 1 mg to about 25 mg, and increased if necessary up to from about 200 mg to about 2000 mg per day as either a single dose or divided doses, depending on the subject's global response.

The azophenol ERG inhibitor compounds according to the invention may be delivered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration. The inhibitors can be formulated alone or together, in suitable dosage unit formulations containing conventional non-toxic pharmaceutically acceptable carriers, adjuvants and vehicles that are appropriate for each route of administration.

For example, suitable oral compositions in accordance with the invention include, without limitation, tablets, troches, lozenges, aqueous or oily suspensions, dispersible powders or granules, emulsion, hard or soft capsules, syrups or elixirs. Inventive compositions suitable for oral use may be prepared according to any method known to the art for the manufacture of pharmaceutical compositions. For example, liquid formulations of the azophenol compounds can contain one or more agents selected from the group consisting of sweetening agents, flavoring agents, coloring agents and preserving agents in order to provide pharmaceutically elegant and palatable preparations of the azophenol ERG inhibitor.

For tablet compositions, typical non-toxic pharmaceutically acceptable excipients include, without limitation, inert diluents such as calcium carbonate, sodium carbonate, lactose, calcium phosphate or sodium phosphate; granulating and disintegrating agents such as, for example, corn starch, or alginic acid; binding agents such as, for example, starch, gelatin or lubricating agents such as, for example, magnesium stearate, stearic acid or talc. The tablets may be uncoated or, alternatively, they may be coated by known coating techniques to delay disintegration and absorption in the gastrointestinal tract and thereby to provide a sustained therapeutic action over a desired time period.

For example, a time delay material such as glyceryl monostearate or glyceryl distearate may be employed.

Formulations for oral use may also be presented as hard gelatin capsules wherein the active ingredient is mixed with an inert solid diluent such as, for example, calcium carbonate, calcium phosphate or kaolin, or as soft gelatin capsules wherein the active ingredient is mixed with water or an oil medium such as, for example peanut oil, liquid paraffin or olive oil.

For aqueous suspensions the azophenol compound is admixed with excipients suitable for maintaining a stable suspension. Examples of such excipients include, without limitation, sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide such as, for example, lecithin, or condensation products of an alkylene oxide with fatty acids such as, for example, polyoxyethylene stearate, or condensation products of ethylene oxide with long chain aliphatic alcohols such as, for example, heptadecaethyleneoxycetanol, or condensation products of ethylene oxide with partial esters derived from fatty acids and a hexitol such as, for example, polyoxyethylene sorbitol monooleate, or condensation products of ethylene oxide with partial esters derived from fatty acids and hexitol anhydrides such as, for example, polyethylene sorbitan monooleate. The aqueous suspensions may also contain one or more preservatives such as, for example, ethyl or n-propyl p-hydroxybenzoate, one or more coloring agents, one or more flavoring agents, and one or more sweetening agents such as sucrose or saccharin.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water can provide the active ingredient in admixture with a dispersing or wetting agent, suspending agent and one or more preservatives. Suitable dispersing or wetting agents and suspending agents are exemplified by those already mentioned above. Additional excipients such as, for example, sweetening, flavoring and coloring agents, may also be present.

Syrups and elixirs may be formulated with sweetening agents such as, for example, glycerol, propylene glycol, sorbitol or sucrose. Such formulations may also contain a demulcent, a preservative, and flavoring and coloring agents.

Compositions for parenteral administrations are formulated in a sterile medium suitable for intravenous, intramuscular or intrathecal delivery. A sterile injectable preparation of the azophenol compounds may be in the form of a sterile injectable solution or sterile injectable suspension. Nontoxic, parentally acceptable diluents or solvents such as, for example, 1,3-butanediol can be used to formulate the parenteral compositions. Among the acceptable vehicles and solvents that may be employed are water, Ringer's solution and isotonic sodium chloride solution. In addition, sterile oils also can be employed as a solvent or a suspending medium. For this purpose, any bland fixed oil may be employed, including synthetic monoglycerides or diglycerides. In addition, fatty acids such as oleic acid can be used in the preparation of injectables.

Depending on the vehicle used and the concentration of the drug in the formulation, the parenteral formulation can contain other adjuvants such as local anesthetics, preservatives and buffering agents.

EXAMPLES

Cell Lines

Tumor cell lines VCaP, COLO320, KG-1, MOLT4, LNCaP, and MDA Pca2b were obtained from the American Tissue Culture Collection (ATCC; Manassas, Va.). The cells were grown in ATCC-recommended cell culture media under cell growth promoting conditions as recommended by the supplier. Normal cells, such as HUVEC-primary cultures of human umbilical vein endothelial cells and the RWPE1 cell line established from normal adult prostate epithelial cells immortalized with human papilloma virus 18 were also obtained from ATCC. The BPH1 cell line derived from primary epithelial cell cultures immortalized with SV40 large T-antigen, were a gift from Dr. Simon Hayward (Vanderbilt University Medical Center). LAPC4, a metastatic prostate cancer cell line was a gift from Dr. Charles Sawyer (then at UCLA).

Reagents

ERG monoclonal antibody (CPDR ERG-MAb; 9FY, licensed to Biocare Medical, CA) was developed and characterized at the Center for Prostate Disease Research. Antibodies for the androgen receptor (AR; sc-816), glyceraldehyde phosphate dehydrogenase (GAPDH; sc-25778), and α-Tubulin (sc-5286) were purchased from Santa Cruz Biotechnology (Santa Cruz, Calif.). Antibody for prostate specific antigen (PSA; A0562012) was obtained from DakoCytomation (Carpinteria, Calif.). Antibodies for apoptosis (9915S) and cell cycle regulator (9932) sampler kits were purchased from Cell Signaling (Danvers, Mass.). Sheep anti-mouse IgG-HRP (NXA931) and donkey-anti rabbit IgG-HRP (NXA934V) were obtained from GE Health Care, Buckinghamshire, UK. A number of the azophenol compounds were obtained from the Stanford University School of Medicine. Many of the azophenol compounds disclosed herein are known in the prior art, typically for their use as dyes. The published methods for their syntheses represent routes by which the compounds of the invention were prepared.

General Protocol for Screening Inhibitors of the ERG Oncoprotein Expression

The TMPRSS2-ERG fusion positive prostate cancer cell line, VCaP (ATCC), was used to identify the test compound inhibitors of ERG expression. Cells were grown in medium using conditions prescribed by the vendor. VCaP cells in logarithmic growth were seeded in a tissue culture dish at a cell density of $2 \times 10^6$ cells per plate. Following 48 hours incubation at 37° C., cells were exposed for a period of 48 hours with 0, 0.05, 0.25 and 0.5 μM concentrations of each test azophenol compound. The inhibition of ERG expression was evaluated by an In-cell Western blot assay (LI-COR Biosciences, Lincoln, Nebr.) using the ERG specific CPDR ERG-MAb as further described below.

Selection of ERG siRNA as a Positive Control

Small interfering RNA (siRNA) oligo duplexes (5' CGA CAU CCU UCU CUC ACA UAU 3': si-1 (SEQ ID NO: 1); and 5' UGA UGU UGA UAA AGC CUU A 3': si-2 (SEQ ID NO: 2)) against human ERG gene (Gene ID: 2078; Accession: NM_004449), were purchased from Dharmacon (Lafayette, Colo.) and were evaluated as positive controls for use in the ERG expression inhibition screens. Two siRNAs were chosen to primarily rule out off target or non-specific effects. Since both siRNAs showed identical results, si-1 was used in the ERG expression inhibitory studies described below. Anon-targeting (NT) siRNA duplex was used as negative control (D-001206-13-20; Dharmacon, Lafayette, Colo.). Cells were cultured in their respective growth medium for 48 hours prior to transfection using a 50 nM concentration of the NT siRNA or ERG siRNA. Lipofectamine 2000® (Invitrogen, Carlsbad, Calif.) was used for transfection.

General Protocol for Evaluating the Inhibitory Effects of Test Compounds by Western Blot Analysis Inhibition of ERG protein expression by the test compounds were determined by Western blot analysis. The ERG specific monoclonal antibody CPDR ERG-MAb was used as the primary antibody. In brief, Western blot was performed by running a fixed amount of total protein extracted from cell lysates of the treated cells using (4-12% Bis-Tris) gel by electrophoresis, followed by transfer to membrane and incubation with primary antibody and continued with HRP-conjugated secondary antibody. Cultured cells were treated at specific dosages with each of the tested ERG inhibitors. Following incubation of the treated cells for an indicated time period, cells were lysed using Mammalian Protein Extraction Reagent (M-PER; Pierce, Rockford, Ill.) containing a protease inhibitor cocktail and phosphatase inhibitor cocktails I & III (Sigma, St Louis, Mo.). Cell lysates containing 50 μg of total protein were electrophoresed through 4-12% Bis-Tris Gel (Invitrogen, Carlsbad, Calif.) and the cellular proteins were transferred to PVDF membrane (Invitrogen, Carlsbad, Calif.). Membranes were incubated at 4° C. for 12 hours with primary antibodies for AR, PSA, GAPDH, α-Tubulin, apoptosis markers and cell cycle regulators. Following exposure to primary antibodies, the membranes were washed with buffer (3×, 5 minutes each at room temperature) followed by incubation with relevant secondary antibodies for 1 hour at 24° C. Finally, the membranes were washed with buffer and developed using the ECL Western blot detection reagent (GE Health Care, Buckinghamshire, UK). The ERG protein expression of the test azophenol compounds were normalized with GAPDH.

Selective Inhibition of ERG Expression

In brief, ERG positive VCaP cells in loganthmic growth phase were plated in 10 cm tissue culture dish at a cell density of $2 \times 10^6$ cells per dish. The plated cells were treated with 0, 0.2, 0.4, 0.6, 0.8 and 1 μM concentrations of each azophenol compound for a period of 48 hours. Cells from each dish were then processed for Western blot analysis and alterations in the expression of ERG protein were monitored. Both ERG and GAPDH protein band were quantified from each concentration using Image J (NIH) and ERG band density was normalized with corresponding GAPDH protein control. Relative density of ERG in each concentration was calculated and with Graphpad Prism 6 software, the IC50 of each compound was calculated.

General Protocol for Cell Growth and Tumor Growth Inhibition Studies

The appropriate ERG positive cancer cells, control ERG negative cells or ERG positive normal cells were grown as adherent monolayers or suspensions in tissue culture dishes using the appropriate growth medium as suggested by the vendor. Approximately 48 hours following plating of cells, the appropriate test compound is added to each well of the tissue culture dish at a predetermined concentration. The medium was replenished every 24 hours with fresh growth medium containing the same concentration of the same test compound for indicated period of the cell growth inhibition assay. Percent cell growth inhibition was calculated using a hemocytometer for estimating cell density in each of the test wells of the tissue culture dish and trypan blue dye exclusion microscopy and photography to estimate the fraction of viable cells in each test well.

To investigate whether the azophenol compounds selectively arrested the growth of ERG positive cancer cells (VCaP), VCaP cells were cultured to achieve cells in logarithmic growth and these cells were then plated in 6 well tissue culture dishes in duplicates at a cell density of $0.2 \times 10^6$ cells per well. The plated cells were exposed to 0, 0.2, 0.4, 0.6, 0.8 and 1 μM concentrations of each compound for a period of 8 days. At the end of time period, cells were recovered from the test plate, washed, trypsinized and the cell density of viable cells were determined with trypan blue dye staining method and automated cell counter Bio-Rad TC10. The IC50 of cell growth inhibition of each compound was determined by trypsinizing the cells at the end of the experiment and counting the cells by using the automated cell counter (Bio-Rad TC10 automated cell counter). The average cell numbers of each concentration were used to calculate the IC50 of each compound with the GraphPad Prism 6 software.

Male athymic nude mice 6-8 weeks old and weighing 27 to 30 g were purchased from Charles River Laboratories. ERG harboring prostate cancer cells (VCaP) were trypsinized and washed twice with ice-cold PBS, and resuspended in ice-cold 50% matrigel in serum-free DMEM medium. A total of 4×10⁶ cells/0.1 mL/mouse were subcutaneously injected into lower right dorsal flank of the mice. Prior to injection, mice were anesthetized with inhalation anesthesia (isoflurane). Tumor growth was monitored weekly after injection. Three weeks later when tumors were palpable mice were randomly separated into 2 experimental groups and one control group of 7 mice in each group. In the treatment groups, mice were injected intraperitoneally (I.P) with 100 mg/kg of the test compound or 150 mg/kg of the test compound while the control group were injected with vehicle (1:1[v/v], DMSO/PEG300) only. Growth in tumor volume was recorded weekly by digital caliper measurements and tumor volumes calculated using the ½ (L×W$^2$) formula, where L=length of tumor and W=width. Tumor volumes were compared between treated and control groups with repeated measurements and statistical significance of the results between the groups computed using students t-test and p values calculated.

Table 1 below shows the results of testing of azophenol compounds.

| Compound | Cell line | Tissue origin | ERG gene status | ERG protein inhibition (IC50) | Cell growth inhibition (IC50) |
|---|---|---|---|---|---|
| 3 | VCaP | Metastatic prostate cancer | TMPRSS2-ERG fusion; ERG protein (N-33 aa-del) | 1.352 | 4.070 |
| 4 | VCaP | Metastatic prostate cancer | TMPRSS2-ERG fusion; ERG protein (N-33 aa-del) | 1.855 | 1.122 |
| 8 | VCaP | Metastatic prostate cancer | TMPRSS2-ERG fusion; ERG protein (N-33 aa-del) | N/D | N/D |
| 9 | VCaP | Metastatic prostate cancer | TMPRSS2-ERG fusion; ERG protein (N-33 aa-del) | N/D | N/D |
| 10 | VCaP | Metastatic prostate cancer | TMPRSS2-ERG fusion; ERG protein (N-33 aa-del) | N/D | N/D |
| 5 | VCaP | Metastatic prostate cancer | TMPRSS2-ERG fusion; ERG protein (N-33 aa-del) | 0.5422 | 0.5572 |
| 6 | VCaP | Metastatic prostate cancer | TMPRSS2-ERG fusion; ERG protein (N-33 aa-del) | 0.2727 | 0.0739 |
| 7 | VCaP | Metastatic prostate cancer | TMPRSS2-ERG fusion; ERG protein (N-33 aa-del) | 0.5587 | 0.6260 |
| 11 | VCaP | Metastatic prostate cancer | TMPRSS2-ERG fusion; ERG protein (N-33 aa-del) | N/D | N/D |
| 12 | VCaP | Metastatic prostate cancer | TMPRSS2-ERG fusion; ERG protein (N-33 aa-del) | N/D | N/D |
| 13 | VCaP | Metastatic prostate cancer | TMPRSS2-ERG fusion; ERG protein (N-33 aa-del) | N/D | N/D |

N/D: Assay performed, inhibition not detected at the tested levels.

All publications cited herein are incorporated by reference in their entireties.

REFERENCES

Rao et al., 1987a erg, a human ets-related gene on chromosome 21: alternative splicing, polyadenylation, and translation, Science 1987 Aug. 7; 237(4815):635-9. PMID: 3299708

Rao et al., 1987b Expression in *E. coli* of erg: a novel gene in humans related to the ets oncogene, Oncogene Res. 1987; 2(1):95-101.PMID: 2851121

Reddy et al., 1987 The erg gene: a human gene related to the ets oncogene, Proc. Natl. Acad. Sci. U.S.A. 1987 September; 84(17):6131-5. PMID: 347693

Watson et al., 2010 ETS Transcription Factor Expression and Conversion During Prostate and Breast Cancer Progression, The Open Cancer Journal, 2010, 3, 24-39

Sreenath et al., 2011 Oncogenic activation of ERG: A predominant mechanism in prostate cancer, J. Carcinog. 2011; 10:37. doi: 10.4103/1477-3163.91122. Epub 2011 Dec. 31. PMID: 2227942

Dobi et al., Biological and Clinical Implications Androgen-responsive genes in prostate cancer: Regulation function and clinical application (edited by Zhou Wang), Chapter 19: Androgen-dependent oncogenic activation of ETS transcription factors by recurrent gene fusions in prostate cancer. Springer Science & Business Media. LLC2013, BWF Book 300271. New York USA DOI 10.1007/978-1-4614-6182-1_19 (2013)

International Agency for Research of Cancer, WHO, Press Release No 209, Mar. 21, 2012 http://globocan.iarc.fr/old/FactSheets/cancers/prostate-new.asp; http://www.cancer.org/cancer/prostatecancer/detailedguide/prostate-cancer-key-statistics Eur. Urol. 2007 May; 51(5):1175-84. Epub 2007 Jan. 12, Natural history of biochemical recurrence after radical prostatectomy: risk assessment for secondary therapy. Simmons MN1, Stephenson A J, Klein E A.

J. Clin. Oncol. 2011 Sep. 20; 29(27):3659-68. doi: 10.1200/JCO.2011.35.1916. Epub 2011 Aug. 22. Common gene rearrangements in prostate cancer. Rubin MA1, Maher C A, Chinnaiyan A M Chen Y, Chi P, Rockowitz S. Iaquinta P J, Shamu T, Shukla S, Gao D. Sirota I, Carver B S, Wongvipat J, Scher H I, Zheng D, Sawyers C L. Nat. Med. 2013 August; 19(8):1023-9. doi: 10.1038/nm.3216. Epub 2013 Jun. 30

Cancer Cell. 2015 Jun. 8; 27(6):797-808. doi: 10.1016/j.ccell.2015.05.005. ERG Activates the YAP1 Transcriptional Program and Induces the Development of Age-Related Prostate Tumors. Nguyen LT1, Tretiakova MS2, Silvis MR1, Lucas J1, Klezovitch O1, Coleman I1, Bolouri H1, Kutyavin VI1, Morrissey C3, True LD4, Nelson PS5, Vasioukhin V6

EIS rearrangements in prostate cancer. Rubin M A. Asian J. Androl. 2012 May; 14(3):393-9. doi: 10.1038/aja.2011.145. Epub 2012 Apr. 16. Review.

Fabian et al., Nat. Biotechnol. 23, 329-336 (2005)

Angermayr et al., J. Biol. Chem. (1997) 272, 31630-31635

We claim:

1. A pharmaceutical composition comprising a compound selected from:

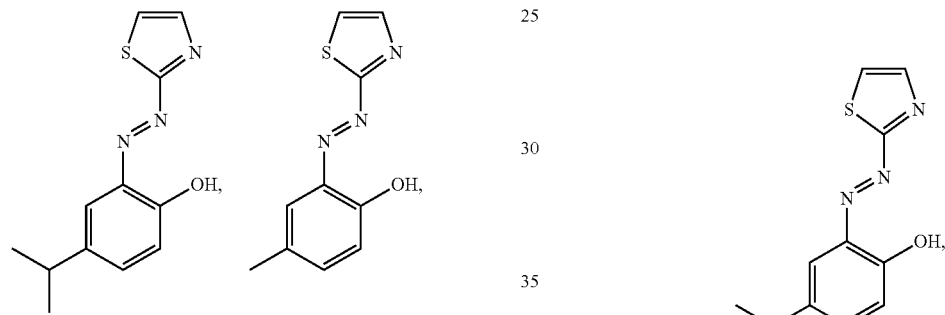

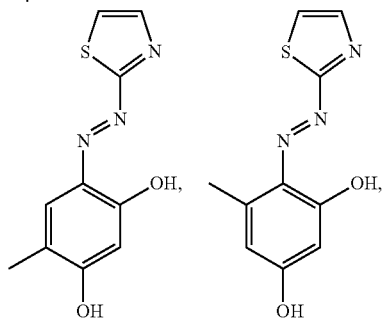

or a pharmaceutically acceptable salt thereof, and an excipient.

2. The pharmaceutical composition according to claim 1, wherein the compound is:

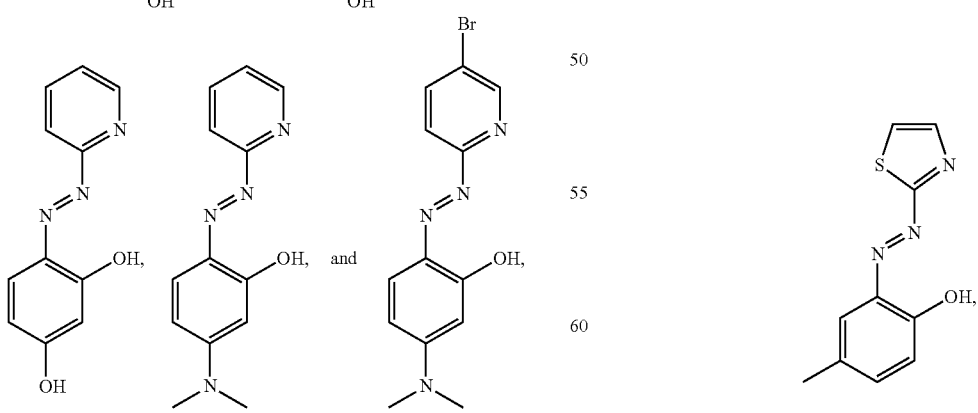

or a pharmaceutically acceptable salt thereof.

3. The pharmaceutical composition according to claim 1, wherein the compound is:

or a pharmaceutically acceptable salt thereof.

4. The pharmaceutical composition according to claim 1, wherein the compound is:

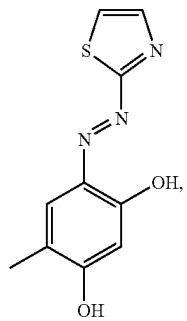 [SMILES: Cc1cc(/N=N/c2nccs2)c(O)cc1O]

or a pharmaceutically acceptable salt thereof.

5. The pharmaceutical composition according to claim 1, wherein the compound is:

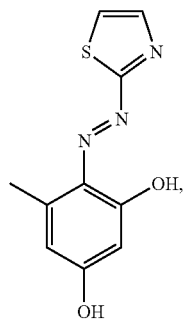 [SMILES: Cc1cc(O)cc(O)c1/N=N/c1nccs1]

or a pharmaceutically acceptable salt thereof.

6. The pharmaceutical composition according to claim 1, wherein the compound is:

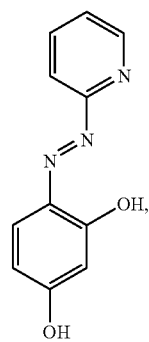 [SMILES: Oc1ccc(/N=N/c2ccccn2)c(O)c1]

or a pharmaceutically acceptable salt thereof.

7. The pharmaceutical composition according to claim 1, wherein the compound is:

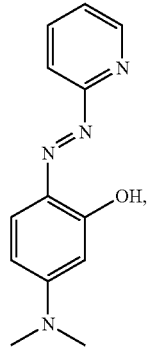 [SMILES: CN(C)c1ccc(/N=N/c2ccccn2)c(O)c1]

or a pharmaceutically acceptable salt thereof.

8. The pharmaceutical composition according to claim 1, wherein the compound is:

or a pharmaceutically acceptable salt thereof.

9. The pharmaceutical composition according to claim 1, further comprising an anti-cancer agent.

10. The pharmaceutical composition according to claim 9, wherein the anti-cancer agent is for prostate cancer.

* * * * *

SEQUENCE LISTING

<160> NUMBER OF SEQ ID NOS: 2

<210> SEQ ID NO 1
<211> LENGTH: 21
<212> TYPE: RNA
<213> ORGANISM: ARTIFICIAL SEQUENCE

```
<220> FEATURE:
<223> OTHER INFORMATION: Synthetic

<400> SEQUENCE: 1
cgacauccuu cucucacaua u                                         21

<210> SEQ ID NO 2
<211> LENGTH: 19
<212> TYPE: RNA
<213> ORGANISM: ARTIFICIAL SEQUENCE
<220> FEATURE:
<223> OTHER INFORMATION: Synthetic

<400> SEQUENCE: 2
ugauguugau aaagccuua                                            19
```